(12) United States Patent
Bullard et al.

(10) Patent No.: US 7,031,843 B1
(45) Date of Patent: Apr. 18, 2006

(54) COMPUTER METHODS AND SYSTEMS FOR DISPLAYING INFORMATION RELATING TO GENE EXPRESSION DATA

(75) Inventors: Brian R. Bullard, Sante Fe, NM (US); Sean Mullins, Ellicott City, MD (US)

(73) Assignee: Gene Logic Inc., Gaithersburg, MD (US)

( * ) Notice: Subject to any disclaimer, the term of this patent is extended or adjusted under 35 U.S.C. 154(b) by 0 days.

(21) Appl. No.: 09/158,982

(22) Filed: Sep. 23, 1998

Related U.S. Application Data

(60) Provisional application No. 60/059,727, filed on Sep. 23, 1997.

(51) Int. Cl.
  *G01N 33/48* (2006.01)
  *C12Q 1/00* (2006.01)
  *C12Q 1/70* (2006.01)
  *G06G 7/48* (2006.01)

(52) U.S. Cl. .................. 702/19; 435/4; 435/6; 702/20; 703/11

(58) Field of Classification Search ............... 435/6, 435/810, 69.1; 422/50, 68.1; 436/501
See application file for complete search history.

(56) References Cited

U.S. PATENT DOCUMENTS 5,599,672 A   2/1997   Liang et al. ................. 435/6
5,811,231 A * 9/1998   Farr et al. ................... 435/6

FOREIGN PATENT DOCUMENTS

WO    WO 97/05286    2/1997

OTHER PUBLICATIONS

Sogawa et al., Proceedings of the National Academy of Sciences, USA., vol. 83, pp. 8044-8048, 1986.*
Rushmore et al., Proceedings of the National Academy of Sciences, USA., vol. 87, pp. 3826-3860, 1990.*
de Groot et al., EMBO Journal, vol. 10, pp. 2523-2532, 1991.*
Stoeckert, Jr. et al., Nature Genetics, 32 (Suppl.), pp. 469-473, 2002.*
Yershov et al. "DNA Analysis and Diagnostics on Oligonucleotide Microchips", Proc. Natl. Acad. Sci. USA (May 1996), vol. 93, pp. 4913-4918.*
Sogawa et al. "Location of Regulatory Elements Responsible for Drug Induction in the Rat Cytochrome P-450 Gene", Biochemistry (Nov. 1985), vol. 83, pp. 8044-8048.*
Rushmore et al. "Regulation of glutathione S-transferase Ya subunit gene expression: Identification of a unique xenobiotic-responsive element controlling inducible expression by planar aromatic compounds", Proc. Natl. Acad. Sci. USA (May 1990), vol. 87, pp. 3826-3830.*
de Groot, et al. "Characterization of the mouse junD promoter—high basal level activity due to an octamer motif", The EMBO Journal (1991), vol. 10, pp. 2523-2532.*
Sockert Jr., et al. "Microarray databases: standards and ontologies", Nature Genetics suppliment, vol. 32., (Dec. 2002), pp. 469-473.*
Lockhart, David J., et al., "Expression monitoring by hybridzation to high-density oligonucleotide arrays", *Nature Biotechnology*, vol. 14, No. 13, Dec. 14, 1996, pp 1675-1680.
Liang, Peng, et al., "Differential Display of Eukaryotic Messenger RNA by Means of the Polymerase Chain Reaction", *Science*, vol. 257, Aug. 14, 1992, pp. 967-971.

(Continued)

*Primary Examiner*—John Brusca
*Assistant Examiner*—Eric DeJong
(74) *Attorney, Agent, or Firm*—Eleanor M. Musick; Procopio Cory Hargreaves & Savitch LLP

(57) ABSTRACT

The invention described herein relates to computer and display methods and systems for acquiring, storing, manipulating, analyzing, linking, retrieving and displaying the data. The methods and systems are illustrated with reference to data on constituents of biological systems, particularly data on gene expression. In this regard, the invention especially relates to interactive systems for displaying gene expression-related data in three-dimensional molecular topographies. Expressed genes and their activity are represented as peaks in the topographies. Additionally, the invention relates to methods and systems for generating and displaying delta plots, which show differences in gene expression, and to methods and systems for generating molecular movies that show changes in gene expression. While illustrated by reference to gene expression, the methods and systems can be used to generate and manipulate displays of data on other complex populations.

20 Claims, 16 Drawing Sheets

OTHER PUBLICATIONS

Spinardi, Laura, et al., "Protocols for an improved detection of point mutations by SSCP", *Nucleic Acids Research*, vol. 19, No. 14, Jul. 25, 1991, p. 4009.

McClelland, Michael, et al., "RNA fingerprinting and differential display using arbitrarily primed pCR", *Trends in Genetics*, vol. 11, No. 6, Jun. 1995. pp. 242-246.

Leuhrsen, Kenneth R., et al., "Analysis of Differential Display RT-PCR Products Using Fluorescent Primers and GENESCAN™ Software", *BioTechniques*, vol. 22, No. 1, Jan. 1997, pp. 168-174.

Jones, Susan W., et al., "Generation of Multiple mRNA Fingerprints Using Fluorescence-Based Differential Display and an Automated DNA Sequence", *BioTechniques*, vol. 22, No. 3, Mar. 1997, pp. 536-543.

Lang, Perg, et al. "Differentia display using one-base anchored oligoed T primers", *Nucleic Acids Research*, vol. 22, No. 25, Dec. 25, 1994, pp 5763-5764.

Ito, Takashi, et al, "Fluorescent differential display arbitrarily primed RT-PCT fingerprinting on an automated DNA sequencer", *FEBS Letters*, vol. 351, No. 2, Sep. 5, 1994. pp. 231-236.

* cited by examiner

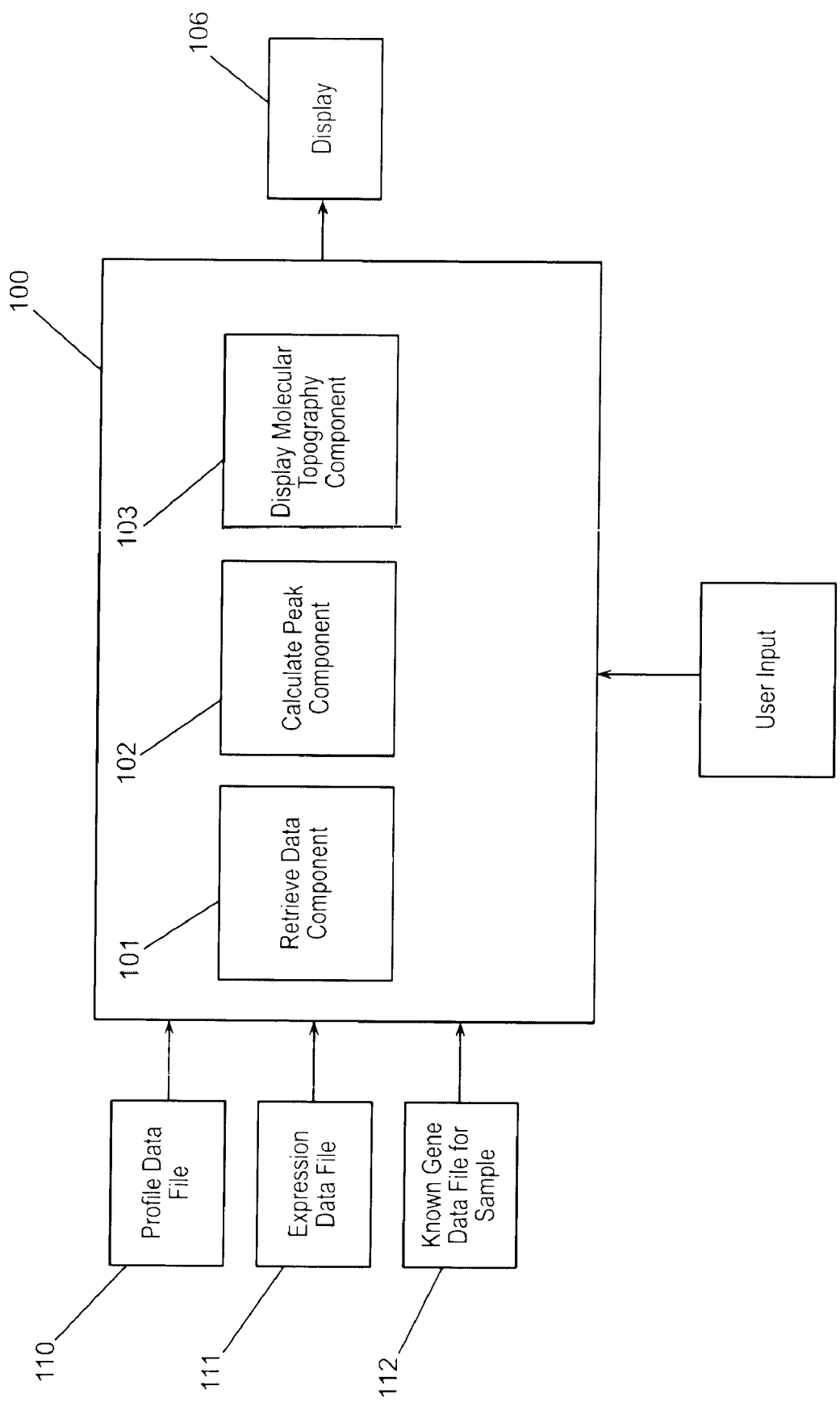

COMPUTER METHODS AND SYSTEMS FOR DISPLAYING INFORMATION RELATING TO GENE EXPRESSION DATA

This application claims the benefit of priority to a provisional application filed on Sep. 23, 1997 and assigned Ser. No. 60/059,727.

TECHNICAL FIELD

The present invention relates generally to computers methods and systems for acquiring, storing, manipulating, comparing, analyzing, displaying and interacting with information relating to gene expression profiles, for linking such profile information to other information, such as information in sequence databases, and for storing, retrieving, manipulating, analyzing, displaying and interacting with the linked information, and for doing so graphically, through profile displays.

BACKGROUND OF THE INVENTION

Computational methods and systems are essential in virtually every area of human endeavor. Often, the limits of a computational system define abilities to acquire, manipulate, analyze, understand or utilize information. This effect is becoming increasingly important in many areas of biochemical research, such as genomics research and research on gene expression. And, although bioinformatics methods and systems are developing rapidly, the volume and complexity of information from sequencing and profiling projects, to mention just two areas, is increasing even more rapidly. Thus, improving the ability of computational methods and systems remains essential to many of the most important areas of biochemical research. For instance, progressively more powerful molecular biology and biochemistry techniques are being used to determine the complete sequences of increasingly larger genomes. Acquiring, storing and making sense of the data produced by genome sequencing in itself poses a challenge to current computational methods and systems. Recently developed methods of profiling gene expression on a large scale likely will produce even more challenging amounts of data. Furthermore, using this information to understand physiology, determination, differentiation, response to environmental factors, embryogenesis development, aging, dysfunction, disease, transformation and death, in simple and complex cells and in complex multicellular organisms poses perhaps the greatest challenge of all.

The challenges to computation methods and systems in biochemistry and molecular biology is briefly illustrated in more detail in the following discussion of work on genome sequences and work on expression profiling.

The techniques of molecular biology and biochemistry are being applied to determine the structures and mechanisms of genetic information and control of physiology, determination, differentiation, response to environmental factors, embryogenesis, development, aging, dysfunction, disease, transformation and death in cells and in multicellular organisms, to name just a few areas of research.

Powerful techniques for accurately determining the exact sequence of bases in fragments of DNA several hundred bases in length have been available since the late 1970s. Initially, these techniques were laboriously applied to determine the complete sequences of relatively small plasmid and viral genomes, such as pBR322, polyoma virus and SV40, as well as individually isolated genes, such as immunoglobulin and globin genes of various species, interferons and cytokines to name just a few.

More recently, DNA sequencing methods have been automated and applied to sequencing entire genomes of more complex organism. For instance, the complete sequence of a mycoplasma, of one prokaryote from each of three major evolutionary branches, the sequence of *E. coli* and the sequence of a yeast all have been completely determined. Work to determine the complete sequences of much more complex genomes, including simple plants and animals and, especially the human genome, is progressing rapidly and it is likely that the complete sequence of the human genome will be known within a relatively short span of years.

More powerful sequencing techniques under development will make it possible to determine DNA sequences rapidly and accurately in the clinical laboratory, as a diagnostic tool. And, it is likely that miniaturized implementations of one or more sequencing techniques will provide automated sequencers with throughputs on the order of millions of base pairs per hour. Such devices could be used to determine, very quickly, the entire sequence of mitochondrial DNA in a patient blood sample, for instance, or to determine the profile of a million polymorphisms in a patient's genome. It is even conceivable that the time is not long off when the DNA of every patient will be sequenced as a matter of course in its entirety, allowing rapid acquisition of genetic predispositions.

Similarly, the miniaturization of these automated techniques will make it possible to screen other organisms for many purposes, using a complete genome sequence. In the health care setting this will make it possible to identify infectious agents and to identify tumor types with unparalleled speed and accuracy. It will allow testing for drug resistance, and for response to therapeutic agents and regimens. It will make possible a greater degree of therapeutic tailoring of therapies to individual patients and disease circumstances. Moreover, it will play an important role in drug discovery and the development of new therapies for disease, to mention just a few of the implications of the widespread deployment of such techniques in clinical practice and biomedical research.

However, DNA sequencing provides basically structural information. The vast amount of information that now can be acquired about DNA sequences thus increasingly highlights the need for equally powerful techniques for assessing the activity of genes; i.e., gene expression. Efforts thus are underway to develop methods for determining all the active genes in a cellular sample and for simultaneously classifying the activities.

One type of technique developed toward this end involves hybridization to oligonucleotide arrays. Illustrative of this approach is the method for "Expression monitoring by hybridization to high-density oligonucleotide arrays" described by Lockhart et al. in *Nature Biotechnology* 14: 1675–1680 (1996).

Another approach to expression monitoring is the technique of differential display, described by Liang and Pardee in their paper "Differential Display of Eukaryotic Messenger RNA by Means of the Polymerase Chain Reaction" in *Science* 257: 967–971 (1992) and in U.S. Pat. No. 5,599,672 of Liang et al. (See also *Nuc. Acids Res.* 19: 4009 et seq. (1994) or *Trends Genet.* 11: 242 et seq. (1995)). Numerous variations and improvements on the basic differential display technique have been published, as well. For instance, Luehrsen et al. described the "Analysis of Differential Display RT-PCR Products Using Fluorescent Primers and "GENESCAN" Software" in *BioTechniques* 22: 168–174

(1997). And Jones et al. described the "Generation of Multiple mRNA Fingerprints Using Fluorescence-Based Differential Display and an Automated DNA Sequencer" in *BioTechniques* 22: 536–227 (1977), to name just two examples in this regard.

These techniques presently suffer from several disadvantages. Perhaps most important is their limited quantitative reproducibility, which leads to a significant incidence of false positive signals, as much as 80% in the case of differential display. (As described regarding differential display in *Trends Genet.* 11: 242 et seq. (1995), *Nuc. Acids Res.* 22: 5763, et seq. (1994) and *FEBS Lett.* 351: 231 et seq. (1994), among others). Furthermore, the hybridization techniques generally are useful only to analyze expression of genes whose sequences already are known hybridization chip technology has not yet produced arbitrary sequence arrays that could assay the expression complement even of relatively small genomes. Differential display and oligo-chip techniques furthermore suffer from irreproducibility caused by unpredictable hybridization of random short sequence probe sets to high complexity targets under low stringency conditions.

A reproducible technique for profiling gene expression with great quantitative accuracy has been described, more recently. In its most common format, this technique quantitatively determines mRNA abundance in samples by measuring the amounts of 3'-end fragments of cDNAs generated by specific primers and specific cleavage reactions. The technique is described in detail in pending PCT patent application number PCT/US96/12468, published as WIPO publication WO97/05286, dated 13 Feb. 1997, the disclosure of which is incorporated herein, in its entirety.

However, the very power of the gene expression profiling techniques poses a challenge to data handling methods and systems, to methods and systems for manipulating and analyzing the data, and to methods and systems for displaying the data so that it can be comprehended, studied and used. That is, the DNA sequence and gene monitoring techniques produce enormous amounts of data, so much so that new techniques are necessary for handling the data, for making it useful and for manipulating, analyzing and displaying it.

A single copy of a human genome, for instance, contains about 3,300,000,000 base pairs, encoding about 100,000 genes. About 15,000 genes are active in any given type of cell, very roughly. Each active gene gives rise to at least one corresponding mRNA. The expression of 15,000 different active genes thus gives rise to more than 15,000 different corresponding mRNAs. Also, genes have greatly varying activity. In consequence, the 15,000 different types of mRNA are present in greatly differing amounts. Thus, gene expression in a given human cell results in a very large pool of mRNA molecules, made up of greatly varying amounts of about 15,000 different types of mRNA, corresponding to roughly 15,000 different active genes. Gene expression can be assessed by determining the different types of mRNA that are present in a cell or tissue and the amount of each type. One complete profile of gene expression in a cell is provided by determining all the types of mRNA in a cell and the amounts of each one. As noted above, for a human cell this involves about 15,000 different mRNAs. To determine differences in gene expression in a cell or tissue, or changes in gene expression over time, numerous profiles must be determined and compared.

Moreover, information from profiling experiments can have its greatest effect only when it is combined with information from other research. Thus, information from profiling experiments for greatest effect should be linked to information in DNA sequence data banks and information about characterized genes, mRNAs, proteins and the like. For greatest utility, linkage between profiling information, DNA sequence information and other information about genes, gene expression, expressed proteins, cell phenotypes and genotypes and organismal physiology and disease (to name just a few categories) should be linked on an mRNA by mRNA basis, so that all the information pertaining to a given mRNA (or representative thereof) in a gene expression profile can be retrieved readily and interactively.

A variety of techniques have been developed for storing, manipulating, analyzing and displaying DNA sequence information. Such techniques are described in many journal articles and books, such as SEQUENCE ANALYSIS PRIMER, Gribskov and Devereux, Eds., UWBC Biotechnical Resource Series, Stockton Press, New York (1991) and GUIDE TO HUMAN GENOME COMPUTING, Martin J. Bishop, Ed., Academic Press, Inc. Harcourt Brace & Company, Publishers, San Diego (1994). For the most part these techniques relate to the acquisition, formatting, storage, manipulation and analysis of DNA sequence information. These genomics methods and systems are designed particularly for managing experimental data from sequencing projects, for sequence assembly, for assembling sequences into "contigs," for developing physical maps of DNAs and whole genomes, for sequence comparisons, for sequence functional inference and for genetic linkage analysis. Although powerful, these techniques generally are not useful for many purposes associated with expression profiling.

In contrast to the many bioinformatics techniques that have been developed for DNA sequencing and sequence analysis applications, presently there are few or no such techniques available for many purposes of gene expression profiling. Furthermore, the few techniques that are available suffer from many limitations and disadvantages, such as the lack of a flexible user interface, the lack of a flexible display paradigm that effective portrays to users the results of profiling experiments, the lack of an interactive display that the enables users to carry out and to visualize the results of a wide variety of data analysis approaches to gene expression profiling data, the lack of an interactive display that allows users to access information about mRNAs and genes represented in displays through a graphical user interface that links defined parts of a graphical display, e.g., peaks, to information in linked records, the lack of effective tools for generating records and databases and linking them to profiles and profile displays, to mention a few shortcomings of present bioinformatics methods and systems for acquiring, storing, manipulating, analyzing, comparing, linking and displaying gene expression profiling data. There is therefore a need for efficient, flexible, powerful, interactive methods and systems for storing, organizing, retrieving, manipulating, analyzing and displaying gene expression profiling data and related information.

SUMMARY OF THE INVENTION

Therefore, it is a general object of the invention to alleviate the needs and shortcomings identified above.

These and other objectives are achieved by providing a method in a computer system for analyzing and displaying data on gene expression in a molecular topography, comprising:

(a) generating a gene expression profile of a plurality of gene-expression indicating polynucleotides including for each of the polynucleotides:

(i) a first value for a first polynucleotide characteristic,
(ii) a second value for a second polynucleotide-characteristic different from said first characteristic, and
(iii) a third value that is a measure of the quantity of the polynucleotide;
(b) calculating for each polynucleotide from the first, second and third values, a position and a peak in a multi-dimensional displace space; and
(c) displaying the peak for each polynucleotide at the position for the polynucleotide in the display; the resulting display representing thereby a molecular topography of gene expression.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiments given below, serve to explain the principles of the invention. The figures are merely exemplary and do not portray or define the limits of the invention, per se.

FIG. 2 is a block diagram illustrating the components of a preferred embodiment of the analysis and display system.

FIG. 3 is a block diagram illustrating the generation of the data files.

GLOSSARY

Figure 1:
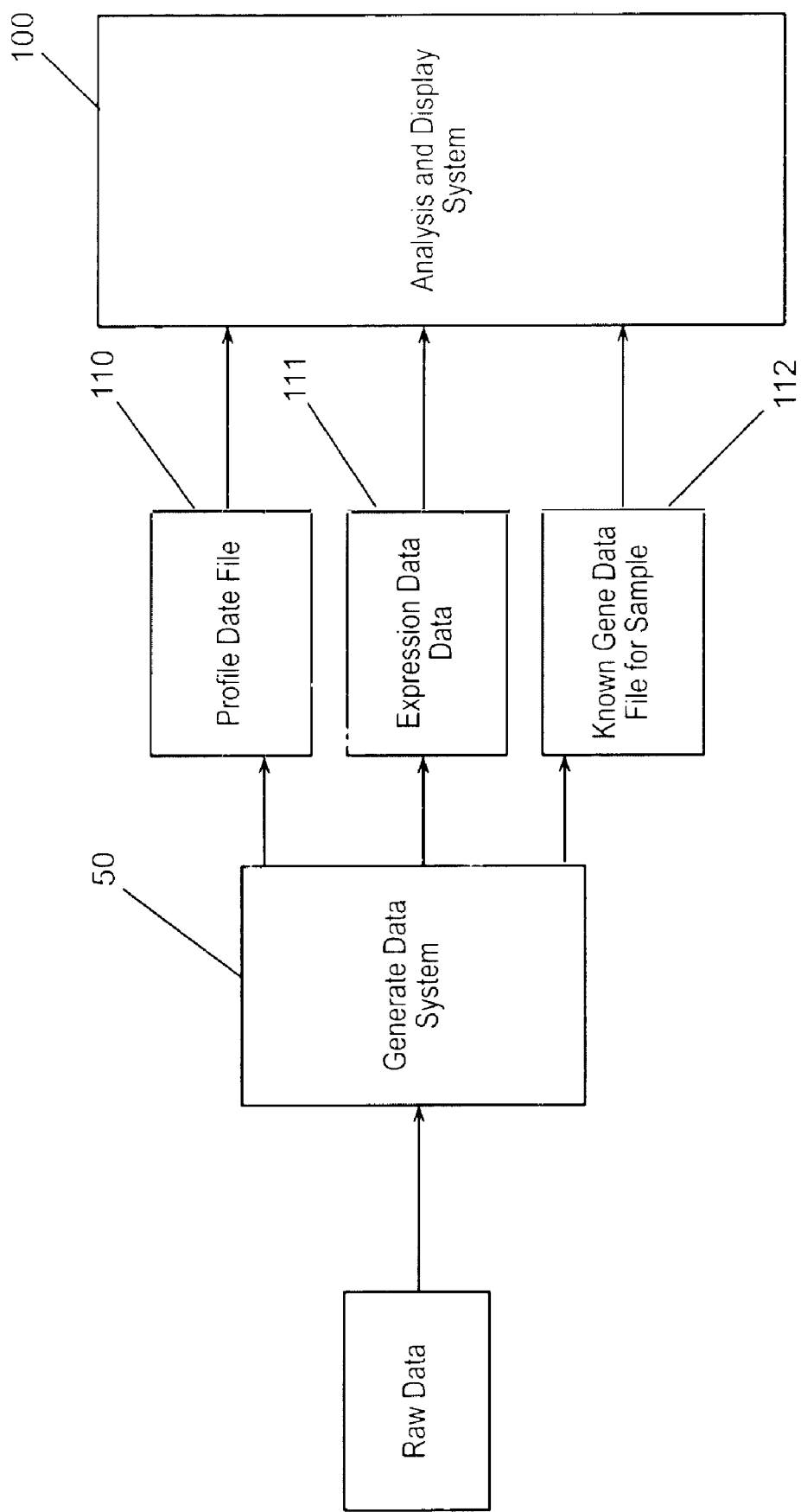
FIG. 1 is block diagram showing the interface between the generated data files and the analysis and display system.
Figure 1:
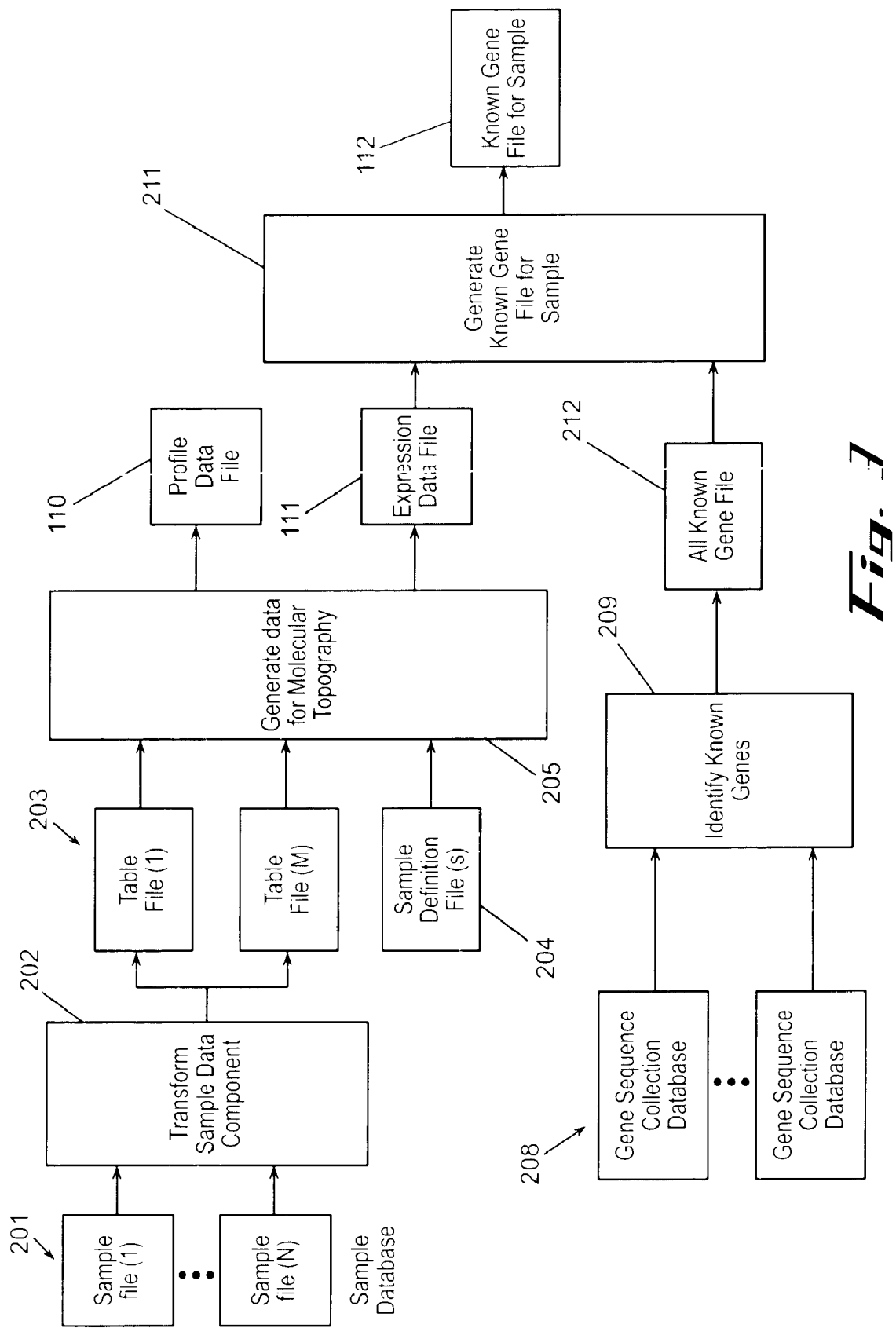

Unless indicated otherwise, terms are used herein in accordance with their meanings in the arts to which they pertain, generally the computer science arts and the arts of biochemistry, molecular biology and genetics. The following glossary is provided as a guide to the meanings of certain terms in the present disclosure. However, the explanations set out below are illustrative, not exhaustive. Indeed, given the nature of the subject matter under discussion, often it is not or possible to provide exhaustive or absolute definitions of useful terms. In sum, the explanations are provided to usefully illuminate but not to limit the scope of the invention. The full meanings of terms used herein and the full scope of the invention can be understood only by careful reading and interpretation of the entire disclosure with the full knowledge and understanding of the person skilled in the arts to which they pertain.

AXIS: See ordinate.

CHRONO-TOPOGRAPHY, CHRONO-TOPOGRAPH: Acquisition, storage, manipulation and display of changes in molecular populations (changes in molecular profiles) over a period of time. Generally, this term relates to acquiring successive datasets on a sample or comparable samples over a period of time and applying molecular topography methods to the datasets to derive, analyze and display (among other things) the temporal changes that occur in the molecular population under study in the sample. Such molecular populations can be or represent mRNAs in the sample. And the successive samples can be of a given cell population over the course of the cell cycle, or of a given cell population before, during and after exposure to an agent, such as a candidate pharmaceutical agent or a known pharmaceutical agent, or a mutagen or a carcinogen, or a physiological effector, to name just a few. The results of chrono-topography often are advantageously displayed in a molecular movie (see below).

CO-ORDINATE: See ordinate.

CORRELATED EXPRESSION, CORRELATED GENES, CORRELATED GENE EXPRESSION: Genes that in some sense are expressed together, or whose expression is related are referred to herein as "correlated gene" and their expression is referred to as correlated gene expression or correlated expression. Included among such correlated genes are, to cite just a very few solely for illustration: genes that are co-regulated, e.g., that respond to regulatory factors in common; genes that encode the proteins of a regulatory cascade, such as the enzymes and co-factors of the blood clot-forming pathways; genes that are expressed in a temporal cascade, where expression of one leads to expression of another, such as the genes involved in the gene expression cascades of differentiation; and genes that encode proteins of related function, such as enzymes of a single metabolic pathway or subunits of a complex macromolecular structure, such as a membrane-spanning pore or a transcription complex.

DYNAMIC TOPOGRAPHY, DYNAMIC TOPOGRAPH: Similar to chrono-topography, but with emphasis on changes in one or more molecular populations (molecular profiles) that represent a response to a stimulus, or the progressive stages or beginning or end points of a process, as opposed to emphasis on the temporal element per se. For gene expression profiling the molecules generally are representative of mRNAs.

DELTA, DIFFERENTIAL OR DIFFERENCE TOPOGRAPHY OR TOPOGRAPH OR DISPLAY OR PLOT: A difference molecular topography (or difference topograph) showing the difference between two molecular populations (between two profiles). Typically, increases from one population to the other appear as upward pointing peaks above a plane and decreases appear as downward pointing peaks below the plane. Delta plots can be used to display many types of binary comparisons, such as the difference between a sample and a standard, or between a sample and an average, or between a sample before and after exposure to an agent, or two points in time of a sample undergoing a change, to name just a few.

GENE EXPRESSION: The expression of genes, in nature a process that generally occurs in cells. The term is used with reference to individual genes or groups of genes. Gene expression in cells typically is different under different conditions and is different in differently differentiated cells. Gene expression also refers to the complement of genes that are active in a cell, and the degree of their activity, or to particular subsets of the full complement.

It is to be understood, that gene activity is reflected in the characteristics of a cell (the cell phenotype and its phenotypic characteristics) not directly but through the production of mRNA. That is, genes are expressed by directing the production of gene-specific mRNA. The mRNA in turn controls the cell's production of proteins, which are the active structural and functional elements of cells. Although, gene expression in one narrow sense refers to the activity of genes in producing mRNA, as a practical matter, the population of mRNA in a cell is accepted as an accurate representation of gene expression. Accordingly, as used herein the term gene expression refers to the complement of active genes and to the practical representation of the active complement by mRNA. In this sense analysis of mRNA is analysis of gene expression.

It is to be understood furthermore that the term gene expression can refer to the whole set of active genes in cells in a sample or any subset of the genes, as will be clear from the context of usage. As noted above, moreover, the term refers not only to direct measurements of transcriptional activity but also, and more practically, to measurements of mRNA, and in some cases, proteins, that generally reflect transcriptional activity and gene expression per se.

These terms also refer to quantitative aspects of the activity of a gene or of a group of genes, per se, as represented by mRNA or other representative molecules.

MOLECULAR MOVIE: A movie showing a succession of molecular topographies (profiles) of a molecular population in a sample or comparable samples. Generally, the succession is temporal and the display rate easily may be adjusted to condense less interesting periods and highlight more interesting periods.

MOLECULAR TOPOGRAPHY: Acquisition, storage, manipulation and display of data that characterize a population of molecules, to provide a molecular profile or y of the population. The data may be primary data about a population of molecules or it may be derived from such primary data relating to one or to more than one population of molecules. The data may be primary data, mathematically derived from primary data, it may relate absolute or relative data or it may be comparative, moreover, the data may be any combination of these, or it may arise in other ways as described in greater detail elsewhere herein.

For example, in certain highly preferred embodiments of the present invention, the data relates to a population of mRNAs that are represented by cDNA fragments characterized by a dinucleotide cDNA primer anchor, restriction enzyme sequence specificity and length. The combination of the dinucleotide and the restriction enzyme specificity define one identifying characteristic of each cDNA fragment. Size provides a second characteristic. The two characteristics are mapped along two orthogonal axes that form an "X-Y plane," and each cDNA fragment in a profile maps to a unique location in the plane. The amount of a fragment in a sample is represented by a peak above its location in the plane, or in certain cases by a peak facing downward from the plane (as in a delta plot, see below) The methods and systems for generating and using such data on mRNA and on gene expression are highly preferred embodiments of methods and systems of molecular topography.

Furthermore, in certain preferred embodiments of the invention the molecular topographies link information from other sources with information in expression profiles so that peaks in an expression profile are associated with potentially pertinent information about genes or proteins or activities or the like they may represent. For example, in certain embodiments of the invention described herein, molecular topography peaks determined by READS analysis are characterized by dinucleotide anchor sequences, restriction enzyme cleavage reaction specificity and length, and DNA sequence databases are searched to identify known DNAs that match these criteria for each peak. In certain preferred embodiments of this type, clicking on a peak in a molecular topography calls up the linked information about known DNA sequences and genes identified in the databases or databases. In the same manner a variety of other information can be linked to the peaks in the molecular topography. Thus, for instance, experimental details can be linked in this way, information from other molecular topographies can be linked this way, information about related DNAs or genes, or gene products, or activities and function of the gene products, evolutionary information, genetic linkage information, annotative information, and the like, to name just a few types of information, all can linked to the peaks in this manner.

MOLECULAR TOPOGRAPHY, MOLECULAR TOPOGRAPH: A display representing the molecular topography of a population of molecules. As noted above, particularly preferred embodiments of the present invention relate to molecular topographies that profile gene expression, particularly molecular topographies of mRNA populations, especially, topographs of cDNA fragments, particularly the 3'-end cDNA fragments of READS analysis. A given molecular topography (or molecular topograph) may represent all of the data from a profile of mRNA, or just some of the data. Typically, in fact, it will be advantageous to display a part of the data on gene expression from a given sample or samples under study. Such data in a given display may be a randomly chosen part of the data or it may be chosen for particular purposes. For instance, a given display may show only data pertaining to a particular gene family or a related set of genes or gene families. Or it may show only the genes for products involved in a particularly metabolic or catabolic process or pathway, or a developmental or disease process, or the like, to name just a few.

It also will be appreciated that a given molecular topography (or topography, representing all the available information about gene expression in a given sample, may represent gene expression in the sample, incompletely, completely or redundantly. That is, the full set of gene expression data available for profiling expression in a given sample may represent only some of the mRNA in the sample. Furthermore, each mRNA it does represent may be represented more than once. For instance, in a topography representing a set of READS-generated data for a given sample, some mRNAs of the sample may not be represented at all, some mRNAs may be represented by a single 3' end fragment and some mRNAs may be represented by more than one 3'-end fragment. A topography (or topograph) based on the full set of data available for a given sample may be referred to as a full or full data set topography or topograph; although, it also may be called a complete data set topography or topograph. Displaying part of such a topography may be called a partial or selected or selective topography or topograph. Further, such a full data set topography (or topograph) may represent every mRNA present in a given sample at least once. In that case, it may said to be a complete topography or complete topograph of the mRNA in the sample. (A partial topography may be complete if it represents only the non-redundant portions of a full data set topography that is complete). One special type of complete topography has one and only one peak for each mRNA in the sample. Such a topography may be referred to as an isomorphous complete topography or topograph. In some circumstances such isomorphous complete topographies are advantageous, as well. However, redundancies of mRNA representation in a topography can be highly advantageous, providing, for instance, internal controls and comparisons.

ORDINATE: As used herein the term ordinate generally means an axis defining a direction or curve in an n-dimensional space, where n can be two, but preferably is three, and can be greater than three as well. Most often, for display n is three.

Ordinates for use in the present invention can be defined by numerical characteristics, such as size or quantity. The values of numerical characteristics generally are progressively arranged on ordinates in the present invention. The arrangement can be increasing or decreasing in either direction. Furthermore, the scale can be linear, logarithmic, square root, or any other of many known scales that have been described and used to display data. Other arrangements may better serve analysis and display of gene expression, even for numerical characteristics. In fact, the arrangement of numerical values along ordinate might be arranged in repeating banks for some display purposes, or might not be entirely sequential.

In addition, ordinates for use in the present invention may be defined by non-numerical characteristics, such as sequence identifiers. Non-numerical values can be arranged on these ordinates arbitrarily, according to a non-numerical ordering principle or according to a numerical ordering derived from non-numerical values. For instance, sequence identifiers can be ordered by alphabetization. In that case, anchor sequences could be arranged alphabetically and restriction enzyme-related sequence identifiers could be arranged alphabetically by the name of the restriction enzyme or, alternatively, by the alphabetical order of the restriction enzyme recognition site. Anchor sequences or restriction enzymes also could be assigned numbers and ordered numerically.

In other words, a variety of schemes can be used in the invention to order values along an ordinate associated with a characteristic.

In certain of the most highly preferred embodiments of the present invention the display ordinates in the X-Y plane indicate different, independent characteristics of mRNAs or cDNAs, particularly sequence identifiers on one ordinate and a measure of size on the other.

PEAK: A shape for display in an n-dimensional display space, where n is any number of two or more, but typically is three. A peak of the present invention generally is indicative of quantity. Operationally, in certain preferred embodiments of the present invention, a peak is derived from or corresponds to the shape of a band identified by analysis of polynucleotides representative of gene expression. In certain very highly preferred embodiments in this regard, peaks are derived from or correspond to bands (or peaks) generated by automated DNA sequencing devices. Peaks calculated from such data may reflect solely the height of intensity of the fluorescent signal associated with a band, or it may reflect the area under the band associated with a fragment or it may reflect other aspects of the fluorescence of a given band as it moves past the detector. Thus, it may reflect peak spreading or splitting, as well as peak height, as well as integrated peak area. In fact, many techniques that are known for interpreting these and similar signals may be usefully employed in the present invention as the basis of calculating peaks for display in gene expression profiles.

Likewise, many techniques for generating and using peaks in a display to depict the make up of complex populations also are useful in the present invention to generate effective displays of gene expression profiles. The peaks can have any shape useful for showing, analyzing or using the data. For instance, peak heights in a molecular topography may be plotted on an ordinate that indicates the fluorescence intensity linearly, that indicates the log of the intensity, that indicates the square root of the intensity, or that relates to measures of quantity in other ways that may be useful for displaying, using, analyzing or understanding gene expression and other types of data.

POLYNUCLEOTIDE(S): DNA, mRNA, oligonucleotides, and the like, including naturally occurring, modified and synthetic polynucleotides, derivatives thereof, and analogs thereof, among others.

SEQUENCE: Generally, the linear order of bases in DNA or RNA or the linear order of amino acids in a protein. The bases in DNA generally are abbreviated A, T, G and C, in accordance with standard practice in the art. The bases in RNA may be abbreviated the same way, for brevity. However, RNA contains uridine instead of thymidine and, most properly, U should be used in place of T in RNA sequence. The distinction is important chemically, but generally is of no significance to sequences per se, since U and T function much the same in hybridization. Conventionally, sequences are displayed with the 5' base, generally considered the first base, on the left and the 3' base, generally considered the last base, on the right. Since the two strands of double-stranded DNA are "anti-parallel," when the upper strand is displayed conventionally, the lower strand will run in the opposite direction, with the 3' end on the left and the 5' beginning on the right.

SEQUENCE SPECIFICITY: Any sequence that is specific to one or more nucleic acids (RNA, mRNA or DNA). The specificity need serve only to distinguish one or more nucleic acids from other nucleic acids in a useful way. Such specificity generally is based on one or more sequences within the nucleic acid or nucleic acids as they occur in a sample. However, the specificity also may result from manipulations of the sample nucleic acids. Primers of defined sequence generally bind to target nucleic acids in a sequence specific manner, for instance, and restriction enzymes generally cleave double-stranded DNA with sequence specificity—at short restriction enzyme recognition sites. Sequence specificity can may be conferred and built up by using combinations or successive applications or both of two or more sequence specific agents. Thus, sequence specificity can be conferred by one primer, or by several different primers, by one restriction enzyme, or by several restriction enzymes, or by a combination of one or more primers and one or more restriction enzymes, to name a few possibilities.

SEQUENCE IDENTIFIER(S): Sequences that characterize a nucleic acid or a group of nucleic acids. A sequence identifier can be one continuous sequence or it can be a combination of non-continuous sequences. Moreover, a given continuous sequence in a sequence identifier can be a unique sequence or it can be several sequences, such a mixture of all the "degenerate" sequences that can encode a given amino acid sequence. Examples of sequence identifiers are anchor sequences at the 3' end of oligonucleotide primers, recognition sites for a restriction enzymes, combinations of anchor sequences, combinations of recognition sites, and combinations of anchor sequences and recognition sites. Similarly, any primer sequence can serve as a sequence identifier, as can sequences cleaved specifically by other sequence-specific cleaving agents, such as triple-helix forming chelates and intercalating polymers. It is to be appreciated that the sequence of a sequence identifier need not be known exactly, or at all. For instance, any restriction enzyme that reproducibly cleaves DNA at specific sequences can provide a sequences identifier, even if the sequence of the recognition site is not known. The presence of the site itself, particularly when it is manifest by enzyme cleavage, can serve as the sequence identifier.

SIZE: A variety of terms commonly are employed by those of skill in referring to DNA or RNA sizes in particular, and many of the terms are used herein. Generally, size denotes length in bases or base pairs and is used to refer in a generic way to molecular weight, length, migration distance or rate of migration in any process that separates by size, inter alia.

SPECIFICITY OF CLEAVAGE REACTION: Sequence specific cleavage reactions can serve as sequence identifiers, either alone or in combination with other sequence identifiers. The sequence specificity of the cleavage reaction provides the sequence identifying characteristic, even if the cleavage sequence itself is not known. Any sequence specific cleavage agent could be used in this regard. However, most typically restriction enzymes are used, because they are commercially available, relatively inexpensive and reliable. For instance, in certain embodiments of the READS technique for gene expression profiling cDNAs representing mRNAs in a sample are cleaved to generate shorter 3' end fragments that can be separated cleanly from one another, accurately sized and quantitated on instruments designed for automated DNA sequencing. The cDNA fragments can be generated by cleavage with single restriction enzymes or with mixtures of enzymes. Moreover, the recognition and cleavage sites of the enzymes or enzymes may or may not be known. So long as the cleavage reaction reliably provides for sequence-specific recognition and cleavage it can serve as a sequence identifier.

X-Y PLANE: In certain preferred embodiments of the invention gene expression profile information is displayed in a 3-dimensional space defined by three axis. In these especially preferred embodiments, the amount of the cDNA fragments in a topography is indicated along one axis, arbitrarily denoted the Z axis, the size of the fragments is indicated along a second axis, arbitrarily denoted the Y axis, and the sequence identifiers of the fragments are identified along the third axis, arbitrarily denoted the X axis. The different types of cDNA fragments are identified by the combination of sequence identifier and fragment size. Thus, the different mRNAs in molecular topologies of this type are defined by locations in the X-Y plane. Generically, therefore, the X-Y plane denotes the plane or other aspect of a display in which mRNAs are represented distinct from one another. This aspect of a display often is distinct from the aspect indicating the amount of each mRNA. Of course, the identity and the amounts of mRNAs generally are represented by cDNAs or cDNA fragments or other mRNA-derived products.

DETAILED DESCRIPTION

The present invention relates to, inter alia, methods and systems for acquiring, identifying, linking, storing, organizing, retrieving, manipulating and analyzing data relating to constituents of biological samples, and to methods and systems for displaying data, the results of manipulation of data and the results of analysis of data relating to constituents of biological samples.

In another particular aspect, the present invention relates to, inter alia, methods and systems for acquiring, identifying, linking, storing, organizing, retrieving, manipulating and analyzing data relating to gene expression, and to methods and systems for displaying such data, for displaying data relating to gene expression, and results of manipulating and analyzing such data.

In a preferred aspect, the present invention relates to, inter alia, methods and systems for acquiring, identifying, linking, storing, organizing, retrieving, manipulating and analyzing data relating to DNA or RNA or both DNA and RNA of a DNA or RNA-containing sample or samples, or a sample or samples containing both DNA and RNA, and to methods and systems for displaying such data and for displaying results of manipulating and analyzing data relating to DNA or RNA or both DNA or RNA of a DNA or RNA-containing sample, or a sample containing both DNA and RNA. In this respect, the methods and systems of the present invention relate to data on known and unknown DNA or RNA or both DNA and RNA of a sample or samples.

In a particularly preferred aspect of the invention in this regard, the present invention relates to, inter alia, methods and systems for acquiring, identifying, linking, storing, organizing, retrieving, manipulating and analyzing data relating to mRNA in an mRNA-containing sample or samples, such as a biological sample or samples, and to methods and systems for displaying data, the results of manipulation of data and the results of analysis of data relating to mRNA in an mRNA-containing sample or samples, such as a biological sample or samples. In this respect the invention relates to both data on known and unknown mRNAs and to mixtures of known and unknown mRNAs.

In this particular aspect, the present invention also relates to methods and systems for graphically displaying data about mRNA. In a highly preferred aspect in this regard, the invention relates to methods of generating a graphical representation of data about mRNA, such as quantitative data on the mRNA in an mRNA-containing sample or samples, or data derived from quantitative data on the mRNA in one or more mRNA-containing samples, and, in further particularly preferred aspect of the invention, and for displaying information related to data about expressed mRNA via the graphical display of expression data.

A particularly highly preferred aspect relates to graphical display of such data in a three dimensional space defined by three orthogonal ordinates: one for sequence identifiers that characterize one or more mRNAs or fragments thereof; one for absolute or relative size of mRNAs or of fragments thereof, or a property derived therefrom or indicative thereof; and one for the absolute or relative amount of mRNA or mRNAs, or a property derived thereof or indicative thereof. In a further particularly preferred aspect of the invention in this regard, the system links potentially pertinent experimental, gene expression and other information to each peak for display. As set out in greater detail elsewhere herein the ordinate for sequence identifiers and the size ordinate define a plane in which mRNAs (or fragments thereof) of an mRNA-containing sample or samples can be uniquely located by characteristic combinations of sequence identifier and size. The amount of each mRNA in such displays, in especially preferred embodiments in this regard, appear as peaks above or below the X-Y plane in which mRNAs are identified by position.

In such displays the peak area or the peak height, or another peak characteristic may correspond to the quantity of each mRNA. The shape of the peak may be determined using any of a variety of known mathematical techniques for generating shapes representative of quantities. In some preferred embodiments of this aspect of the present invention, peak shapes are directly derived from gel scanning data.

It is to be appreciated that a variety of other visual indications also may be used in this regard, including color properties, such as color, hue, tint, density and brightness. Visual effects such as blinking, also can be used to highlight certain quantitative aspects of such displays.

Each peak in the display can be linked to related information for interactive retrieval. In preferred aspects of the invention linked information can be retrieved and displayed by pointing to a peak with a cursor and "clicking" or executing a cursor-driven command or the like. The linked information in preferred embodiments of the invention can be, inter alia, information about the sample material represented in the display, details of experimental procedures and results pertinent to the data represented in the display, information from databases potentially pertinent to peaks in the display, such as information from DNA sequence databases, particularly information about partial or complete DNA sequences of genes with identifiers that match identifiers of peaks in the display and information related to such partial or complete gene sequences, including published and unpublished information, bibliographic information and the like, information from related experiments, such as related gene expression profiling experiments, regarding particular peaks in the display or the overall pattern of peaks in a partial of full molecular topography, and annotative information, such as that added by those responsible for producing a given topography or for programs that identify and link information to a topography, or information provided by other users.

In certain very highly preferred aspects of the invention in this regard, the linked information comprises the results of DNA database searches that match database gene sequences with peaks in a molecular topography, by matching identifiers. Thus, for instance, in certain preferred embodiments relating to READS-generated gene expression profiles, the data bases are searched for sequences of poly-adenylated mRNAs (preferably derived from cDNAs), the dinucleotides at the poly A junction in the sequences are matched to a dinucleotide anchor of the READS primer, the sequences are scanned for restriction sites for the specific cleavage reactions used to generate the READS profile in question, and the predicted fragment lengths are compared to the lengths of fragments in the corresponding dinucleotide—restriction enzyme cleavage portion of the display. Information about partial or complete gene sequences that give rise to a predicted fragment matching a display fragment is linked to the fragment peak, so that it can be called up by the user through the peak in the display—as by moving the cursor to the peak and clicking. As noted above, certain preferred embodiments of the invention relate to methods and systems for acquiring, identifying, linking, storing, organizing, retrieving, manipulating and analyzing data relating to gene expression and to methods and systems for displaying the data, the results of manipulation of data, the results of analysis of data in the form of molecular topographies and to linking to the display, so that it can be accessed by the user through the graphical interface, or by other means, information relating to the displayed data generally, information relating to specific aspects of the topography and, among other things, information pertaining to specific peaks in the topography, such as information about known genes that are matched with a peak by comparison of identifying characteristics, such as sequence identifiers and fragment lengths.

In preferred aspects of the invention in this regard, the topographies display the amounts of individual DNA fragments, typically fragments of cDNA, as three-dimensional peaks above, or below, a two dimensional plane. In certain particularly preferred embodiments of the present invention in this regard, the distance from the plane to the tip of the peak, or the area of the peak, quantitatively represents the amount of a fragment in the sample. A variety of measures of quantity may be used in this regard, including absolute and relative measures of quantity, as described elsewhere herein in greater detail.

In another respect, in certain particularly preferred embodiments of the present invention, the X-Y plane is defined by two orthogonal axes that display independent fragment identifying characteristics. Thus, in certain highly particularly preferred embodiments in this regard, one axis displays specific sequences that distinguish fragments and the second axis displays the size of each fragment. Thus, in certain specific illustrative embodiments in this respect, one axis displays dinucleotide anchor sequences of primers used for cDNA synthesis and, typically for each anchor sequence, a set of restriction enzymes used to cut the cDNA and generate the fragments. In these embodiments, the combination of anchor and restriction cut provides a sequence-specific characteristic of each fragment that is displayed on a first axis. The length of each separately detected fragment having a given such sequence characteristic is displayed along a second axis, orthogonal to the first axis. Sequence character and length together thus together define location in the two dimensional plane defined by the two axes. Finally, the amount of each fragment is displayed by a "peak" above or below the X-Y plane.

The methods and systems of the invention further provide for interactive manipulation of data associated with molecular topographies. Thus, methods and systems of the invention can for, for instance, assemble constructed molecular topographies that represent pooled data, averaged data, corrected data or the like, or any other type of data that can be derived from original experimental data. Such "constructed" topographies can serve as references in research and clinical applications of the methods and systems of the invention, for instance.

Furthermore, methods and systems of the present invention also provide a flexible user interface for manipulating the display of molecular topographies. Interfaces in accordance with this aspect of the invention provide for displaying part or all of the data associated with a given molecular topography, for altering a given display of data, for instance, by rotation, zooming, switching the directions of ordinates, altering the scale of ordinates, and the like, to name only a few. Many of these graphics display and manipulation capabilities can be derived from or used within readily available and well known graphics packages, adapted to work with the data and files described herein.

As noted elsewhere the methods and systems of the invention provide for interactive access to linked files by the interaction, for instance, of a pointer with peaks in the display. Pointing similarly can be used to alter the appearance of specific peaks in the display, giving them, for instance, a different color or texture. Such off-setting also can be done by sub-routines that identify and highlight peaks that match user-defined criteria. Also, according to methods and systems of the invention, several topographies can be displayed at once on a screen. And, for another example, the order of sequence-identifiers can be arranged along the ordinate in ways set by the user, so as to place, for instance, peaks of greater interest in front and peaks of greater interest in back.

Indeed, in some preferred embodiments of certain aspects of the invention, peaks can be selected for display individually or in groups and displayed independently of other peaks in a molecular topography. Such groupings can be culled from several molecular topographies and then aligned with one another to show the changes that occur in the underlying gene expression under changing conditions represented by the topographies. These features and many others can be used by users in almost an infinite number of way as tools for visualizing, analyzing, understanding and displaying aspects of molecular topographies and the data on which they are based.

Although highly preferred embodiments of the present invention relate to cDNAs (and thereby to mRNAs), it is to be appreciated that the present methods and systems may be used to display information about other molecules, such as DNA, proteins, lipids, carbohydrates, small organic molecules and other constituents of samples, particularly biological samples (i.e., samples of or derived from subcellular, cellular or multicellular organisms, living or dead.) In these embodiments as well, information from a variety of sources, including procedural information and information from database searches, as noted above for mRNA/cDNA gene expression displays, preferably is linked to peaks in the display so that it can be accessed by the user simply by "clicking" on a peak or otherwise indicating that information linked to a particular peak in the display is of interest.

Thus, for instance, the three dimensional display system described above may also be used to display allelic polymorphisms in DNA of a DNA-containing sample or samples. In certain preferred embodiments in this regard one ordinate is for sequence identifiers, another ordinate is for DNA fragment sizes and a third ordinate is for quantity. Thus, for instance, the results of bank of restriction fragment length polymorphism ("RFLP") determinations for one or more samples can be graphically displayed. Of course, inherited polymorphisms generally are the same in all cells of an individual organism and, for diploid organisms, a given polymorphism will be, on a relative scale, either zero, one or two (none if the genome lacks the polymorphism, one if the polymorphism is heterozygous and two if it is homozygous). For RFLP-related data on individuals, thus, the graphical display can be optimized for such "quantized" data. It will be appreciated that each gene will contain either one or two of the potential allelic variants at each polymorphism site and this will be reflected in the display. However, the same technique might be applied to a mixed population sample in alleles exhibit varying penetrance. Given equal representation of the DNA of each individual in the mixed sample, the distribution of many alleles in a population might be simultaneously assessed by this approach. As described above, information pertaining to such a display as a whole and to particular peaks can be linked to the display overall and to particular peaks, respectively.

Similarly, the n-dimensional display space of molecular topographies of the present invention can be defined by a variety of characteristics indicated along an axis. Thus, for instance, a three dimensional display space of the present invention may be defined by three axes, one of which relates to such identifying sequences in DNA of mRNA of a sample as repeat sequences, motifs related to cis-acting or trans-acting control elements, specific mutations of mitochondrial or genomic DNA, characteristic motifs, such as motifs associated with particular types and functions of proteins, sequences defined by primers or by specific cleavage, and other such structural or functional sequence-specific DNA or mRNA characteristics.

Illustrative Example Relating to Gene Expression Profiling Using "READS," Linked Experimental and Known Gene Data, and a Customized Software Suite for Analysis and Display Systems and methods of the present invention are particularly useful for acquiring, identifying, linking, storing, organizing, retrieving, manipulating and analyzing expression profiles obtained by READS and similar quantitative measures of gene expression. The following discussion illustrates the methods and systems of the invention as applied specifically to acquiring, identifying, linking, storing, organizing, retrieving, manipulating, analyzing and displaying data from READS profiling experiments.

It is to be understood, however, that the present invention is not limited to the preferred embodiments described further herein. Rather, the system described in the preferred embodiment can be extended by skilled in the art to encompass the several aspects of the present invention that have been described, supra, in the present application.

As presently carried out for gene expression profiling by analysis of mRNA, the preferred READS method reproducibly sub-divides the mRNA of a sample in a sequence-specific manner into smaller sub-samples. Sequence-specificity comes first from the "primer" that is used to produce cDNA for analysis. Typically, READS analysis often proceeds using a priming step using 12 dinucleotide anchors that divide the sample into twelve sub-samples.

The cDNAs in each sub-sample are then cut with enzymes that act on specific short sequences, typically four bases or six bases long. The fragments resulting from enzyme cleavage then are sorted by size and quantitated. Practically, in certain preferred aspect of the READS technique, the reactions are carried out so that only the 3' end fragments of the cDNA are detected or analyzed. Generally, this is because the label is incorporated only into the 3'-end fragments. Typically, the fragments take the form of "bands" upon separation by gel electrophoresis. Peaks usually are produced as a data stream from a detector measuring fluorescence as peaks travel through the gel and past the detector window or the peaks can be derived by digitally processing an image of fluorescence in the gel as a whole. In both cases, the speed or distance of migration of each peak indicates the fragment size, the peak shape provides information about homogeneity of fragments in a given fluoresced peak, and the peak height and area indicate the amount of the fragment in the sample.

Samples can thus be divided into subsamples not only by carrying out physically isolated analyses for each of the 12 dinucleotide anchors, but also by using distinct and independently detectable labels for each anchor. Highly preferred in this regard are fluorescent dyes used in automated DNA sequencing instruments, which typically provide four different colors: red, blue, yellow and green, as illustrated in the discussion below with reference to the figures. The analysis for four such differently labeled primers then can be carried simultaneously in a single set of reactions and a single gel lane.

Typically, "raw" information from the analysis of fragments is stored in one or more primary files. The primary files typically will contain information not only about the fluorescence peak shape, intensity, migration rate and relative position, for instance, but also information identifying the source of the mRNA, facts about its storage or properties, how it was processed, the details of primer-labeling, the identity and or sequences of the primer or primers used for cDNA synthesis, and the primers and restriction enzymes used to generate the material in each peak, gel lane, gel and set of gels, as appropriate. Thus, data in the primary files generally will include the "raw" output from the detector, or from a dedicated device such as a DNA sequencer, or both. It may be a photograph or digital representation of the signal in the gel, or it may be the detector trace of peaks and retention times. The primary files also will include information that provides additional information about the analysis. This aspect of the invention is illustrated below with reference to the figures and a particularized embodiment of the invention. Primary files that specifically relate to READS carried out using an ABI sequencer are illustrated in the discussion of the figures. Other experimental designs and other instruments may dictate different types of primary files.

The primary file is used to generate one or more secondary files. A secondary file often provides a list of band size and intensity, and peak shape for each band. The band listing may be the same as the raw output of the gel detector or image analysis system, or it may result from processing of the primary data to increase sensitivity or signal to noise ratio or for other purposes. The listing also includes the identity of the primer (sequence) and the restriction enzyme or enzymes used in the cDNA synthesis and the restriction reaction, for each band, either individually or by group.

Various tertiary files can be generated from the secondary files, or the primary files, of both. Moreover, such tertiary files may contain information involving primary, secondary or tertiary files containing data from the same sample, from different samples or from other "mixed" tertiary files. Thus, for instance, tertiary files may contain a listing of band size and intensity and peak shape generated by subtracting the information in this regard in the secondary files for two different samples. Such samples may, for instance, be from normal and diseased states of a given cell type, and the resulting difference thus representative of the differences in mRNA profile and gene expression between the normal and the same disease state. Similarly, cells in quiescent, inhibited or activated states can be compared, and such comparisons can be used to profile the effects of compounds, compositions and formulations of the later mRNA profile and gene expression of cells. Further, the time course of such responses can be determined and the resulting series profiles (or difference profiles) can be viewed in sequence as a "molecular movie" useful to observe dynamic changes in mRNA profile and gene expression over time.

The foregoing files can be used alone or in various combinations to generate a display file for graphical display of profile data and for manipulation by the user to facilitate analysis (among other things).

In addition, in preferred embodiments of the invention, the topography-generating secondary files and the display-generating tertiary files are linked to supplemental files that provide a variety of additional information. In certain highly preferred embodiments of the invention in this regard, certain information in the supplementary files pertinent to specific peaks in the molecular topography is linked to the respective peaks for display to the user. In especially preferred embodiments in this regard, the display system and the linkage provide an interactive interface to the user so that supplemental information pertaining to a peak in a molecular topography can be accessed by a placing a cursor over the peak and entering a command, such as a clicking a mouse button or the like.

The present invention thus provides a computer method and system for analyzing and displaying gene expression developed, for example, by using READS analysis so that a researcher can visually manipulate and analyze the profile.

In certain preferred READS embodiments, an analysis and display system generates a molecular topography for display based on a gene expression profile that includes data for each fragment from the READS profiling experiments. Thus, the READS gene expression data contains, as noted above, sizes and fluorescence intensities of cDNA fragments generated by specific anchors and specific restriction enzyme cleavage reactions.

The system then calculates a peak for each cDNA fragment, based on the fragment's fluorescent signal, for display along the Z ordinate at the location of the fragment in the X-Y plane formed by ordinates for anchor/restriction enzyme specificity and fragment size. Generally, for READS profiling, the peak height corresponds to the height of the corresponding fluorescent signal, and the Z axis indicates peak height, the log of peak height or the square root of peak height. The shape of the peak can be chosen arbitrarily.

The system then displays a visual representation of the peaks in the three dimensional space formed by the X, Y and Z ordinates. That is, the system displays a visual representation of a set of peaks each representing a cDNA fragment in the READS expression data. Each peak indicates: (1) the quantity of a cDNA fragment by its height along a Z axis; (2) the anchor/restriction enzyme reaction used to generate the fragment along the Y axis, and (3) the length of the fragment along the X axis. The resulting three-dimensional image graphically represents the gene expression profile of the cell, and is referred to as a "molecular topography" or "molecular topography In the example noted above for READS data above, each quantity is visually represented as a "peak" within a three dimensional molecular topography. That is, the quantity is represented by a feature of the peak along the Z axis. While the foregoing example mentions only height, quantity can also be represented by area, volume, intensity, coloration, or the shape of the peak. Likewise, these other features of the peak can be used to display additional properties of the polynucleotide fragments in combination with the displayed indication of the quantity.

The system also provides a user interface through which a user can quickly and interactively access additional information about each fragment. The system thus allows a user to select any peak within the molecular topography by, for example, using a conventional selection device, to manipulate the peak or obtain additional information relating to the cDNA fragment represented by the peak. The selection device can include a pointing device such as a mouse or laser pen, a keyboard, and the like.

The system then identifies the fragment corresponding to that peak (i.e., identifies the associated characteristics such as the anchor/restriction enzyme combination and length of the fragment) and displays information relevant to that identified fragment. If the combination of the associated anchor/restriction enzyme and the length corresponds to a known gene, then the system displays information relating to that known gene.

In this regard, it is worth noting that, in preferred embodiments relating to READS, as well as other systems for gene expression profiling, inter alia, the system correlates fragments, identified by the anchor/restriction enzyme combinations and fragment lengths to genes that have been previously identified and catalogued or information about which is available. The system performs this correlation by first analyzing various catalogued databases of information, such as, for example, the Unique Human Gene Sequence Collection ("UniGene") of the National Center for Biotechnology Information ("NCBI"). The system analyzes the databases to identify genes that would produce fragments observed in the gene expression profile. Thus, for READS analysis the databases are searched to (1) identify polyadenylated mRNA or cDNA sequences; (2) identify the dinucleotides at the polyA junction in these sequence; (3) identify the lengths of $3^1$-end fragments produced by restriction enzyme cleavage reactions used to produce the READS gene expression data. The search results then are correlated to the READS data, so that when gene expression profile data is received, the system determines database entries that match fragments in the profile data. The system then links the search results to the READS data so that a user can recall or access information about matches for a specific fragment by clicking on a peak. A variety of information can be linked to READS data in this way, including experimental details, information from previous READS profiles (or profiles generated using other methods) and annotations by information providers, scientists who produced the data, other users and the like, to name a few.

As noted above, methods and systems of the invention include methods and systems for displaying several, related molecular topographies, such as a sequence of molecular topographies of a cell over time. A series of molecular topographies show in a sequence is referred to as a "molecular movie." Molecular movies can be used, for instance, to display a progression of changes in the gene expression profiles generated by, for instance, a series of READS experiments. By viewing a molecular movie, a user can analyze and understand changes in gene expression that occur, for instance, in cells undergoing normal processes of growth, differentiation and division, in cells responding to one or more normal and abnormal stimuli, in cells undergoing disease process, and the like, to name a few. Molecular movies also can be used to compare dynamic differences between related gene expression profiles. For instance, molecular movies can be used to compare gene expression over a time course in wild type and mutants of a given cell line (or two or more mutants) to facilitate, for instance, visualization, analysis and understanding gene expression and temporally-regulated cellular processes that differ as a result the mutation(s). Such "movies" can, of course, be displayed in panel form, as well as sequentially, with arbitrarily chosen numbers of "frames" on a given "page."

Methods and systems of the invention, particularly as related to READS and other techniques for gene expression profiling, also can compare peaks, groups of peaks and whole profiles, assess the differences and similarities of peaks in two or more profiles, and assess differences and similarities in groups of peaks or whole profiles. To compare READS profiles, the expression data for two or more profiles typically are analyzed to identify the analogous fragments which are then compared. Methods and systems of the invention provide users with considerable flexibility for choosing the criteria for determining whether fragments are analogous. Generally, for READS data, analogous fragments are those that have the same anchor/restriction enzyme sequence specificity and the same size, or similar sizes, where the degree of required similarity is set by the user. The amount of each fragment in one profile then is subtracted from its analogous fragment in the other profile to generate a difference. The difference molecular topography, or delta plot, is displayed similarly to a molecular topography, except that the peaks indicate differences in amounts of analogous cDNA fragments between the compared profiles. Often, negative values are displayed below the X-Y plane. Peaks without an analogous fragment are displayed above or below the plane unchanged in magnitude (the sign of the peak will depend on which profile was selected from which).

Thus, READS data from cells to be compared, such as reference and test cells, resting and activated cells, healthy and diseased cells, wild type and mutant cells, normal and abnormal cells, different types of cells, cells from different tissues or sources, resting and stimulated T cells, to name just a few examples, can be displayed in a delta plot showing only the differences in gene expression. Of course, the delta plots can be calculated not only for any two profiles but also for a profile and a reference profile, such as a reference based on averaging a set of profiles, or for a variety of other "constructed" profiles that may be useful to a user.

Moreover, differential molecular topographies can be created for a time course of events, to highlight changes in differences between samples over time. Thus, for instance, the progression of events in a T cell after stimulation can be viewed as a molecular movies of delta plots showing the differences between successive READS profiles as the cell activated. In fact, such movies can be made in many other ways as well. For instance, each successive "frame" might represent the delta plot of differences between the resting state and the successive profiles as the cells become activated, or between a reference profile and the other profiles.

The methods and systems of the invention typically display READS profiles, delta plots and movies as three dimensional molecular topographies. However, the visual representations of peaks and calculated differences between analogous peaks, among others, also can be shown in other multi-dimensional coordinate systems in a similar manner. Methods and systems of the invention also can measure or determine the similarities and differences in peaks, groups of peaks or in gene expression profiles generally. Utilities that carry out this function are flexible, and allow users to set methods of calculating similarity or difference and to set threshold values that determine the peaks that will be displayed. In certain preferred embodiments of the invention, as it relates to READS and other quantitative gene expression profiling methods, this feature is particularly useful for comparing molecular topographies for drug discovery-related experiments, for diagnostic purposes and for therapeutic or prognostic purposes. In this regard, difference and similarity determinations and figures of merit can be used to identify agents that affect cell expression to a certain overall extent or in a certain way to a certain extent. It can similarly be used to assess whether a sample represents a normal, abnormal or diseased state of cells or tissue. Likewise, it can be used assess therapy by determining or classifying the effect of a therapeutic regimen or treatment on cells or tissues.

The mathematical methods for making such comparisons, for READS molecular topographies, or molecular topographies based on other methods, can be simple or sophisticated, can utilize some or all the data available for the sample, can be by reference a test sample or a reference profile, or any other suitable, diagnostic comparator. Generally, such comparisons are based on a determination of analogous fragments, a comparison of the amounts of the analogous fragments, a determination of those that have amounts that are "the same" or "similar" or that are otherwise defined to be "biologically equivalent" quantities, generally defined as being within a probabilistically defined "significant" range, and then calculating a measure, or measures, of difference or similarity of the topographies, based on the amounts of some or all of the peaks, and comparison of the amounts of analogous peaks.

EXAMPLES ILLUSTRATED BY THE FIGURES

The following discussion relates to the illustrative embodiments depicted in the figures. The figures illustrate certain preferred general aspects of the present invention as applied to READS analysis of gene expression. The figures and examples discussed below are exemplary. They are provided to aid understanding of the invention in a general way, by reference to specific examples. They do not depict limitations of the invention, however, and should not be so interpreted.

FIG. 1 shows a high-level block diagram depicting major components for generating a molecular topography display and the relationship between them. The generate data system 50 provides information to the molecular topography analysis and display system (MT system) 100 of the present invention. The generate data system 50 processes the "raw" data that is output from a detection system to generate data files that provide the inputs to the MT system 100. The MT system 100 then provides information for display by a display subsystem. The MT system includes a user input subsystem that allows an interactive manipulation and redisplay of data. In certain preferred embodiments the generate data system accesses not only the data depicted in the molecular topography per se but also linked data for display upon user request.

FIG. 2 shows a preferred embodiment of the analysis and display system which is an MT System 100 including components that are designed to graphically display the molecular topography of a cell on a suitable display 106. The MT system 100 includes a retrieve profile data component 101, a calculate peak component 102, and a display molecular topography component 103.

The MT system 100 receives a profile data file 110 for a sample, such as a profile data file for a particular cell type or a particular tissue. The profile data file 110 contains information describing a gene expression profile of the sample. The gene expression profile can include, for example, for each polynucleotide in the profile: a first value that measures a first sequence-specific polynucleotide characteristic, a second value that measures a second, size related, polynucleotide characteristic, and a third value that is a measure a quantity of the polynucleotide fragment.

For READS the data pertains to 3'-end fragments of cDNA, and the data includes information about the anchor sequence and the restriction enzyme reaction used to produce each fragment, the size of each fragment, and the amount of the fragment. Initially, the information may be input to the system from different sources. Typically, READS data comes from an automated sequencing instrument that outputs information about the distribution of bands detected in lanes of a gel. By labeling several primers with fluorescent tags of different colors it is possible in many cases to resolve in a single gel lane the bands for several anchors produced by a given restriction reaction. Thus, READS data often comes off the sequencer as a set of gel lanes, each with a set of colors, each color with a set of fragment sizes and each fragment size with a fluorescence peak height and area. Raw information from the sequencer is used together with information about the samples loaded onto the sequencer to generate data that identifies for each fragment in a given profile, the anchor/restriction enzyme used to generate the fragment, the size of the fragment and the fluorescence of the fragment, as peak height or area or both, or other measure. For linking data, such as known gene information matched to corresponding peaks, the system 100 also receives an expression data file 111 and a known gene file 112 for linking to peaks that represent polynucleotides in the molecular topology.

FIG. 3 is a schematic diagram showing the generation of a typical profile data file 110, an expression data file 111, and a known gene file 112, as discussed further below.

The MT system 100 displays the molecular topography representing the gene expression of the sample on a suitable display 106. The representation displayed is generated by first calculating a peak for each polynucleotide fragment by the calculate peak component 102 based on the data in the profile data file 110 and an optional user preference. Thereafter, the calculated peak is displayed in a multi-dimensional space, typically a three-dimensional space, by the display molecular topography component 103 on the display 106.

The profile data file 110 is generated, as explained above, from information, for a gene expression profile of a cell and includes the quantity, the length, and the associated anchor/restriction enzyme data for each fragment.

The profile data file 110 for the sample, in one exemplary embodiment, contains one record for each polynucleotide fragment length from 0 to 499 for each anchor/restriction enzyme specificity. If 12 dinucleotide anchors are employed for cDNA synthesis, and each of the twelve differently-primed cDNA products is subjected to 30 different restriction enzyme cleavage reactions, there will be 360 different anchor/restriction enzyme combinations Each of these will provide a set of fragment lengths from 0 to 499, and the profile data file 110 will contain 180,000 records. For display purposes, it is advantageous to include empty records to maintain proper spacing of the fragment lengths in the display.

Table 1 displays a portion of an example data structure and content of a profile data file 110.

TABLE 1

| Length | Anchor/Restriction Enzyme | Quantity |
|---|---|---|
| 20 | 7 | 0 |
| 21 | 7 | 0 |
| 22 | 7 | 87 |
| 23 | 7 | 0 |
| 24 | 7 | 0 |
| 25 | 7 | 0 |
| 26 | 7 | 194 |
| 27 | 7 | 103 |
| 28 | 7 | 134 |
| 29 | 7 | 0 |
| 30 | 7 | 0 |
| 31 | 7 | 0 |
| 32 | 7 | 0 |
| 33 | 7 | 87 |
| 34 | 7 | 317 |
| 35 | 7 | 561 |

In Table I, the first column identifies the lengths of the fragment; the second column contains a numerical indication of the anchor/restriction enzyme combination associated with the fragment; and the third column contains a measure of the quantity of the fragment. The excerpted portion shown in Table 1 represents data for fragments with lengths between 20–35, generated by the anchor/restriction enzyme identified by number 7. For example, the fragment with a length of 22 and with the anchor/restriction enzyme combination identified by number 7 has a quantity of 87 units. Also, the fragment with the length of 32 and with the anchor/restriction enzyme combination identified by a number 7 has a quantity of 0, which means that there were no fragments in the gene expression profile for the sample cell with that length and with that anchor/restriction enzyme combination.

It is to be understood that the profile data file 110 could contain data representative of any of the polynucleotide characteristics, as discussed earlier. The particular data structure described is exemplary only and not intended to limit the application as one skilled in the art could suitably modify the data structure to contain data representative of any of the various polynucleotide characteristics identified earlier.

One skilled in the art would also appreciate that different physical and logical formats may be used for the various files of the system. For example, the length need not be stored in each record of the profile data file 110 because the length can be derived from either an index or a position of the record within the profile data file 110.

The exemplary expression data file 111 for a sample contains a record for each fragment with a non-zero quantity, corresponding to a peak. A sample data structure identifying the types of information contained in each record is shown in Table 2.

TABLE 2

Anchor/Restriction enzyme indicator
Length (without heal and adapter)
Terminal N1N2 of primer
Run number
Gel lane number 1
Gel lane number 2 (only in differential plot file)
Condition name 1
Condition name 2 (only in differential plot file)
Color (Blue, Green, Yellow, or Red)
Quantity of fragment (or difference in quantities)

It is to be understood that the expression data file 111 could contain other data representative of the gene expression of the sample. For example, the four colors may be chosen because the data from each gel lane in the present protocol has four color channels each corresponding to a given primer. This number of color channels, and their actual colors, could be suitably modified to reflect both different primers and additional sensitivity of the detection equipment. Therefore, the particular data structure described is exemplary only and not intended to limit the application, as one skilled in the art could modify the data structure to contain other data representative of the gene expression profile of a sample cell.

The known gene file 112 for the sample contains a record for each peak that represents a known gene. A sample data structure identifying the type of information contained in each record is shown in Table 3.

TABLE 3

Labinfo: a text label
Accession number (UNIGENE or user-specific accession number)
Cuts: a text label
3'-end: a text label
Terminal N1N2N3

The calculate peak component 102 of the molecular topography system 100 inputs the profile data file 110 and generates, for example, a three-dimensional peak representation for each polynucleotide fragment in the sample cell. The generated peak representation is then displayed by the display molecular topography component 103 on a suitable computer display 106.

The retrieve data component 101 is capable of receiving user input (i.e., length and anchor/restriction enzyme combination) identifying a particular polynucleotide fragment. The retrieve data component 101 then determines whether there is information in the known gene file for sample 112 related to the identified fragment. If so, the component 101 retrieves for display the information relating to the known gene corresponding to that identified fragment. The component 101 also retrieves for display the information relating to the identified fragment from the expression data file 111 regardless of whether the identified fragment corresponds to a known gene.

FIG. 3 is a block diagram that shows the different components of an embodiment of the generate data system 50 that is used to generate the input files to the MT system 100. The generate data system 50 includes components for the generation of the profile data file 110, the expression data file 111, and the known gene file for sample 112 for a sample.

The generate data system 50 generates the input files from raw data, such as that derived from an electrophoresis gel and a database of known genes. The information for the sample cell that is derived from the electrophoresis gel is provided in one or more sample files 201. For example, a sample file 201 is provided for each lane of the electrophoresis gel. These sample files are examples of the primary file discussed earlier. Likewise, the data contained in these sample files can be stored in a suitably designed database.

It is to be understood that the different components of the generate data system 50 discussed further herein are exemplary only and do not limit the present invention. One skilled in the art would be able to modify the components to take advantage of additional data that may be generated by, for examples, advances in electrophoresis techniques or other data collection advances.

The transform sample data component 202 transforms the data in the sample files 201 to data in table files 203. Each table file 203 contains the information relating to all peaks detected in each lane of the electrophoresis gel for a given color. Thus, for example, there is one table file 203 for each color. Each record in a table file 203 contains information about a single peak. An exemplary sample of the fields in the data structure for the table files 203 is shown in Table 4.

TABLE 4

Gel lane number
Color
    (B, G, Y or R indicating the color Blue, Green, Yellow or Red)
Peak number
Length
Height
Area The peak number is a sequential number indicative of fragments with non-zero quantities, the height indicates the quantity of the fragment (i.e., height of the peak), and the area represents the size of the area of the gel corresponding to that peak. It should be understood that other features of the peaks can be used to represent data indicative of other polynucleotide fragment features. That is, the shape, coloration, area, volume or any other feature of the peak can be used to represent different properties of the polynucleotide fragments.

Table 5 contains example data that may be contained in the table files 203.

TABLE 5

| 1B,14 | 82.76 | 44 | 204 |
| 1B,15 | 118.92 | 45 | 230 |
| 1B,16 | 119.87 | 30 | 171 |
| 1B,17 | 120.96 | 66 | 399 |
| 1B,18 | 122.04 | 153 | 772 |
| 1B,19 | 122.99 | 447 | 2772 |
| 1B,20 | 123.81 | 1358 | 7815 |

The first record of the example data indicates that the data is from lane 1 for the color blue ("B"), corresponds to the 14th peak, has a length of 82.76 (based on "raw" gel migration", a fluorescence peak height of 44, and a fluorescence peak area of 204.

The sample definition file 204 contains a record for each color in each lane. The record identifies a sequence specific polynucleotide characteristic, such as a anchor/restriction enzyme combination, associated with the color and lane.

The generate data for molecular topography component 205 inputs the table files 203 and the sample definition file 204 and generates the profile data file 110 and the expression data file 111 for the sample. The profile data file 110 and the expression data file 111 are, therefore, examples of secondary data files discussed earlier.

The identify known genes component 209 searches through various databases 208 of gene sequences to identify all known genes based on a user selectible or a predetermined criteria. The component 209 stores the identified gene information in the all known gene file 210.

The generate known gene file for sample component 211 inputs the expression data file 111 for a sample and the all known gene file 210 and generates a known gene file 212 for the sample cell.

Figure 4H:
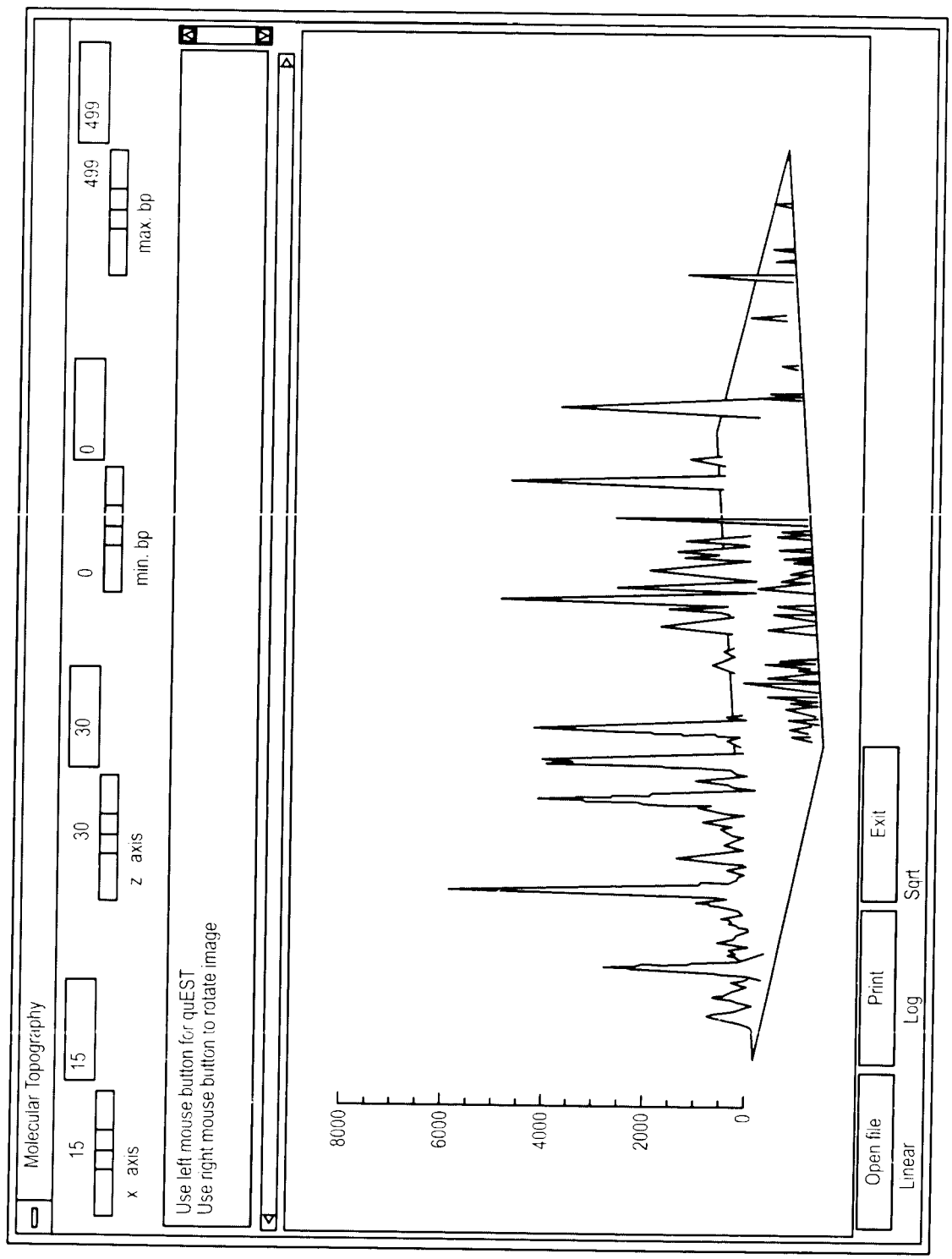
FIG. 4A is a picture of a molecular topography of a resting T cell, displayed in an interactive window.
FIG. 4B is a picture of a molecular topography of an activated T cell, displayed in an interactive window.
FIG. 4C is a picture of a differential molecular topology of the resting and activated T cell topographies of FIGS. 4A and 4B, displayed in an interactive window.
FIG. 4D is a picture showing six views of differential molecular topologies with different orientations to the viewer of the X and the Z ordinates. The picture shows some of the ways in which views can be rotated and manipulated by a user.
FIG. 4E is a picture showing a series of molecular topographies that make up part of a molecular movie. Each topography (from left to right and top to bottom) represents a successive time point in a series of identical assays of gene expression over a period of time.
FIG. 4F is a picture of a differential molecular topography displayed in an interactive window, showing access to linked information for a chosen peak. The chosen peak is topped by a horizontal line. A descriptive excerpt of the linked information is displayed directly above the topography, indicating a database Accession Number for a DNA sequence that contains a fragment matching that of the peak.
Figure 4B:
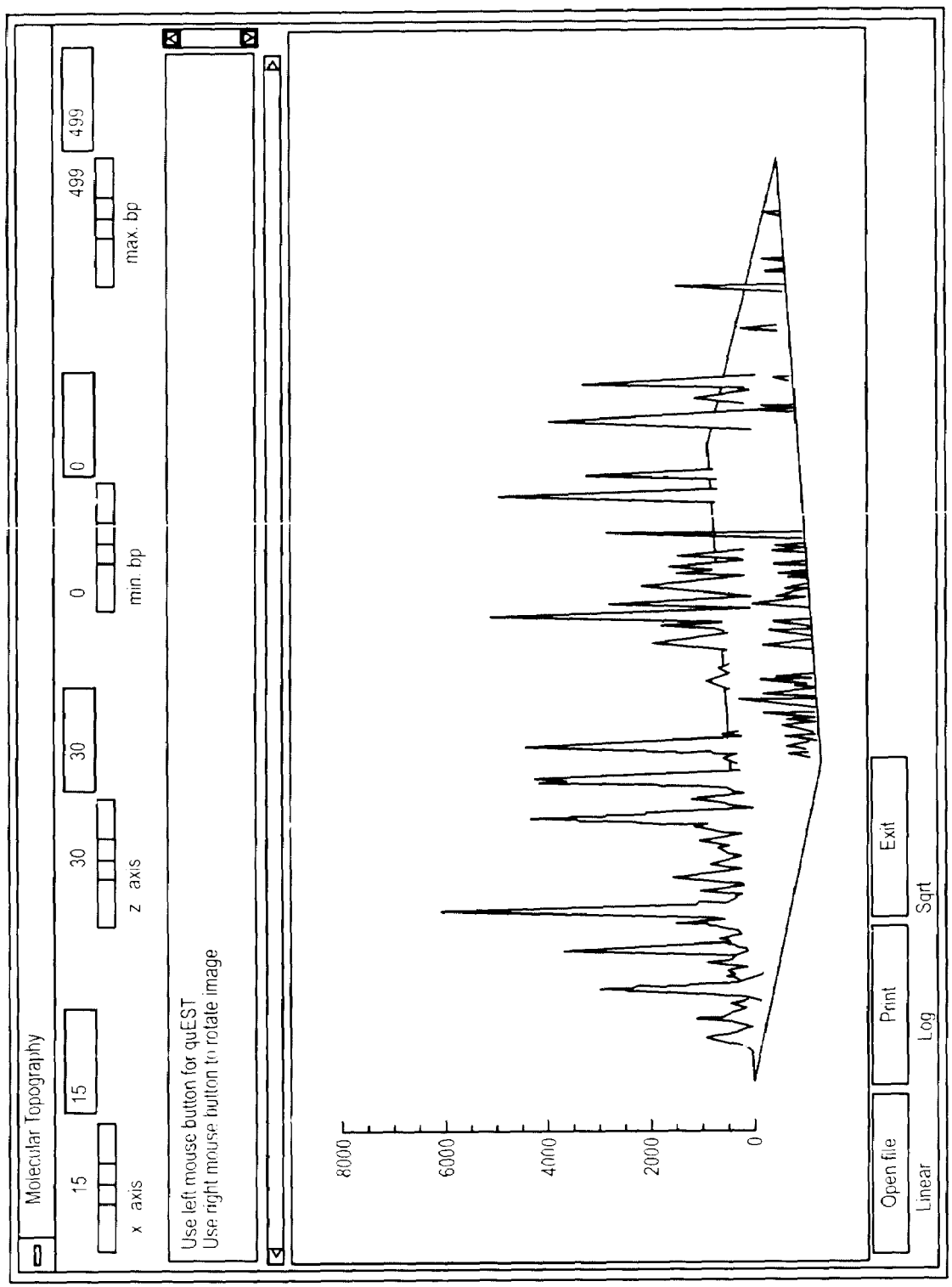

FIGS. 4A and 4B provide exemplary molecular topography displays of gene expression in, respectively, a resting T cell and an activated T cell. In these displays the peaks are mapped along three orthogonal axes. The amount of each fragment is indicated on the vertical ("Z") axis in units of fluorescence intensity from 0 to 8000. The anchor/restriction enzyme combinations are arrayed along the "Y" axis running from the Z axis along the left side of the "X-Y" plane, which is shaded. Fragment sizes are indicated along the "X" axis running across the front of the shaded "X-Y" plane.

Figure 4C:
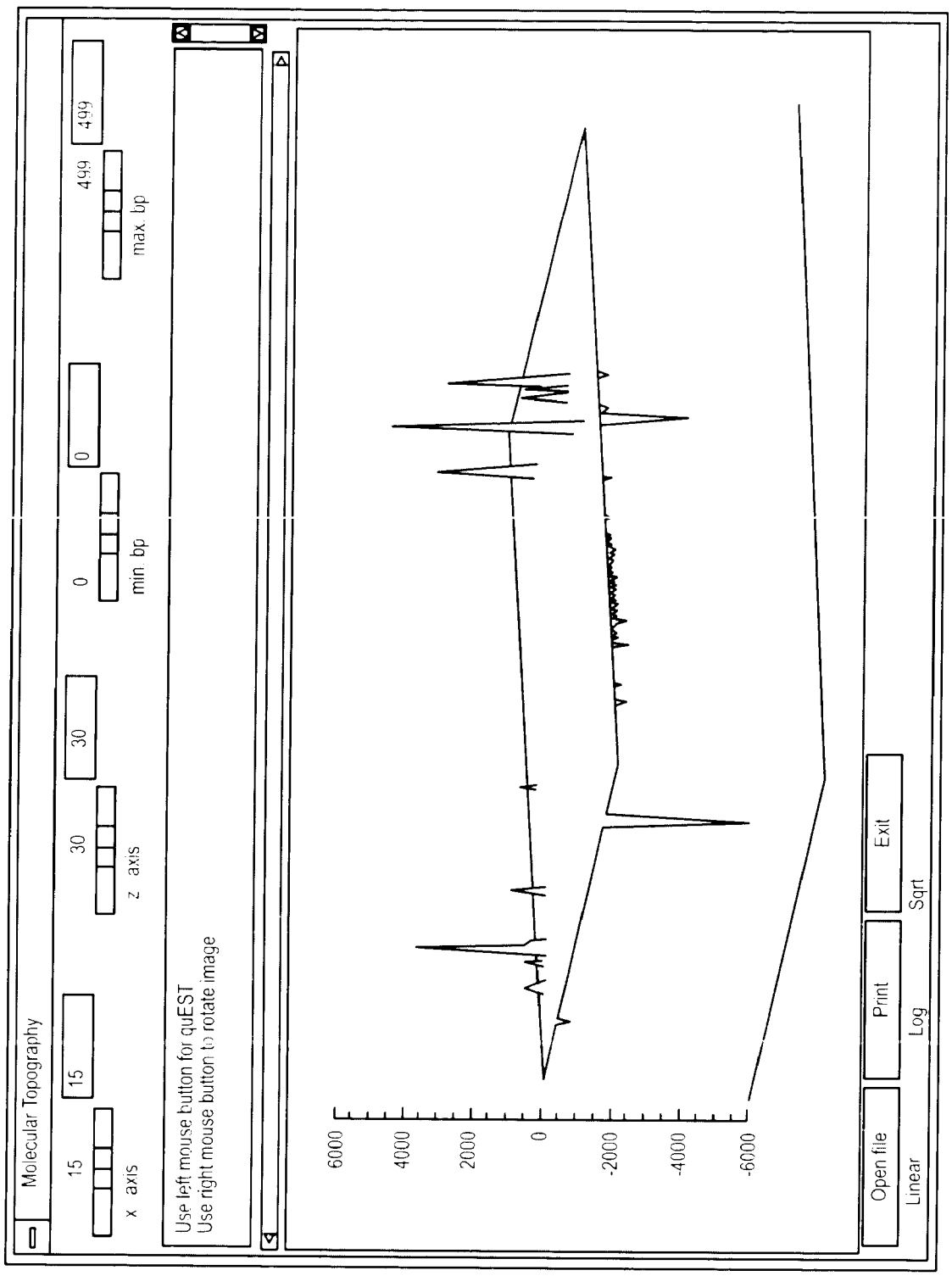

FIG. 4C illustrates a differential molecular topography of the resting and activated T cells shown in FIGS. 4A and 4B. Peaks above the X-Y plane represent genes that are "up-regulated" in the activated cells, while those below the plane represent genes that are "down-regulated."

Figure 4D:
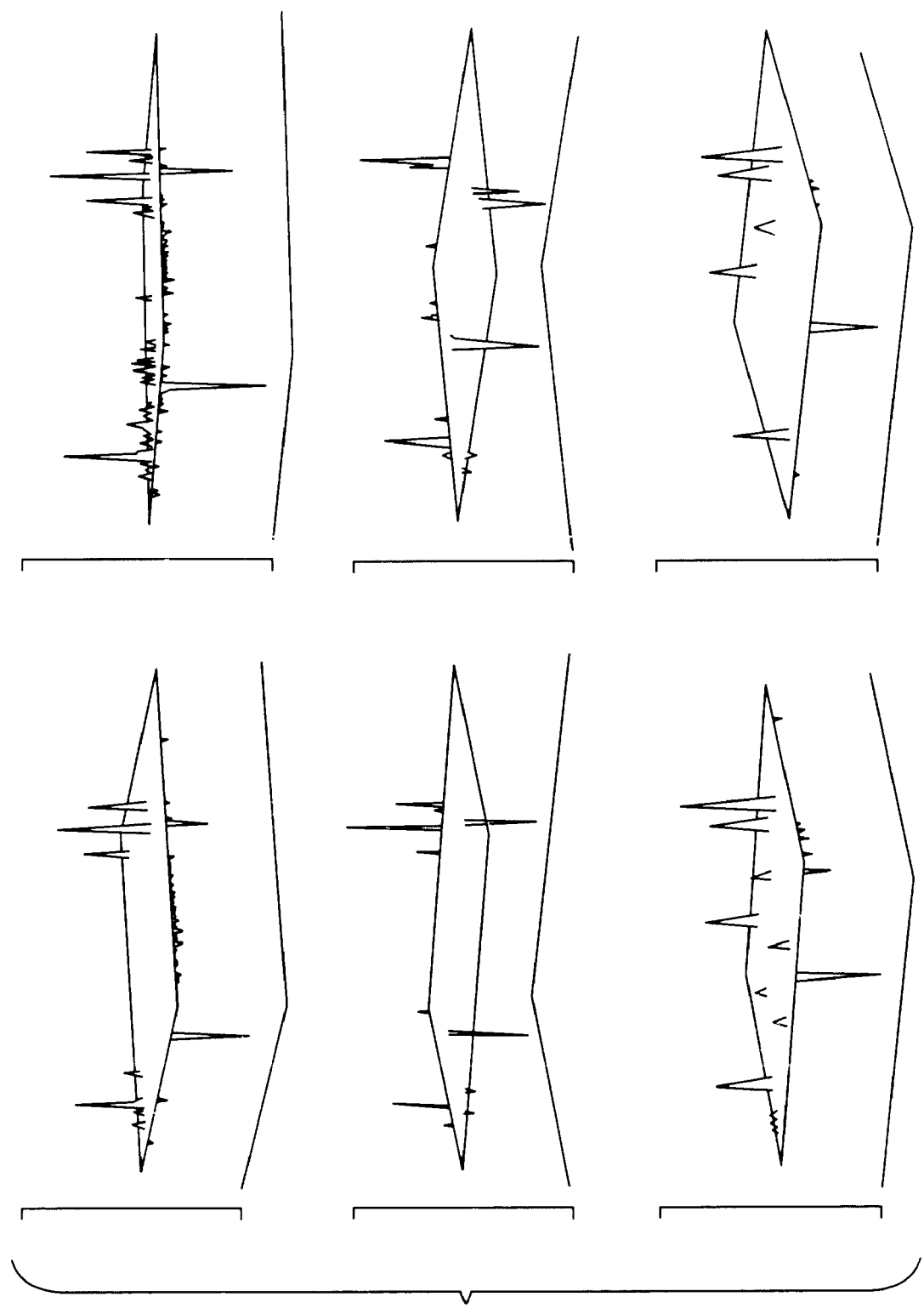

FIG. 4D shows some of the display manipulations that can be performed on a molecular topography, such as those of FIGS. 4A–C. It shows six views of differential molecular topologies oriented differently around the X and the Z ordinates.

Figure 4E:
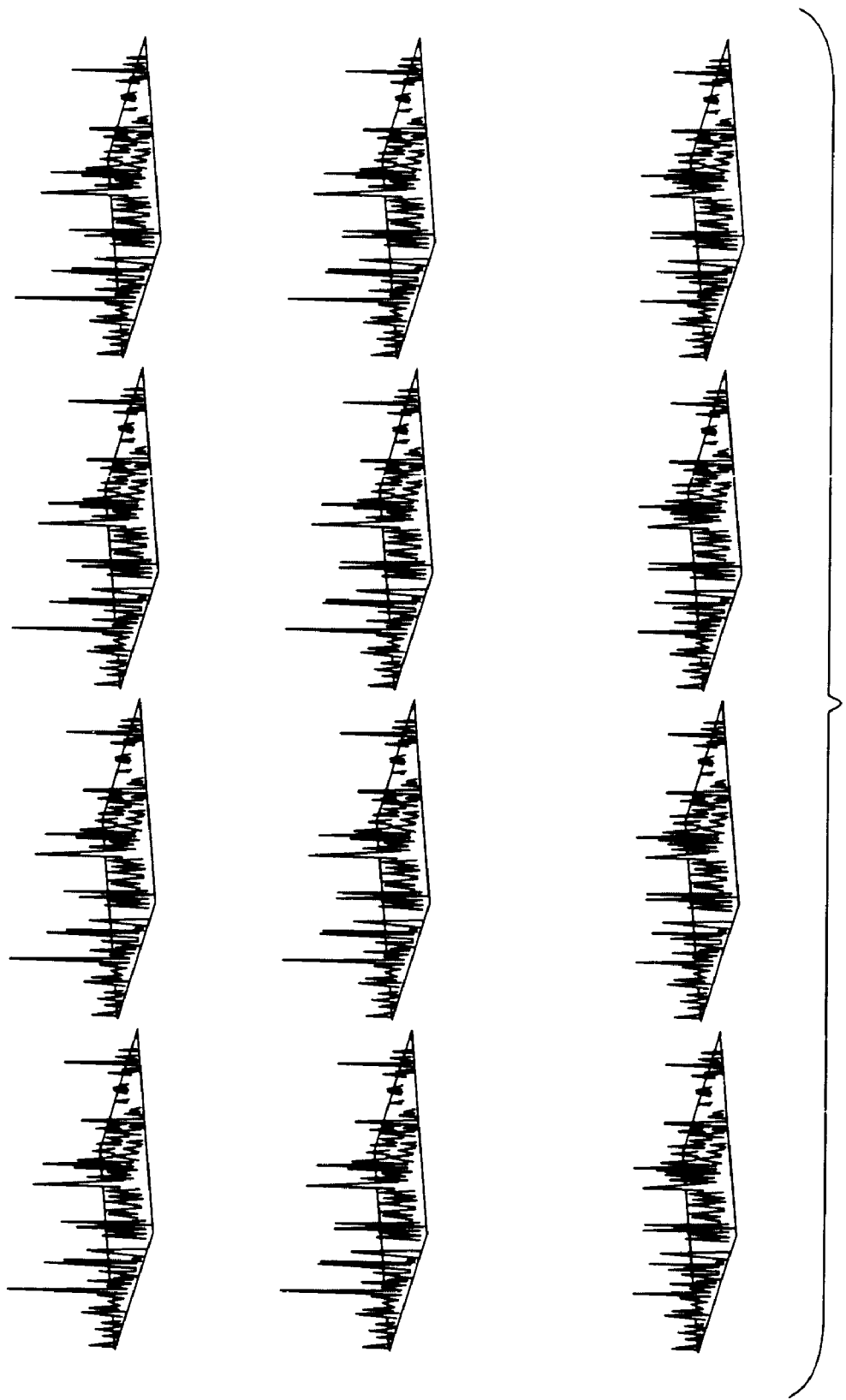

FIG. 4E illustrates a series of molecular topographies that make up part of a molecular movie. Each topography, starting from the upper left and moving from left to right and top to bottom, is a successive time point in a series of identical assays of gene expression of a cell undergoing a change.

Figure 4F:
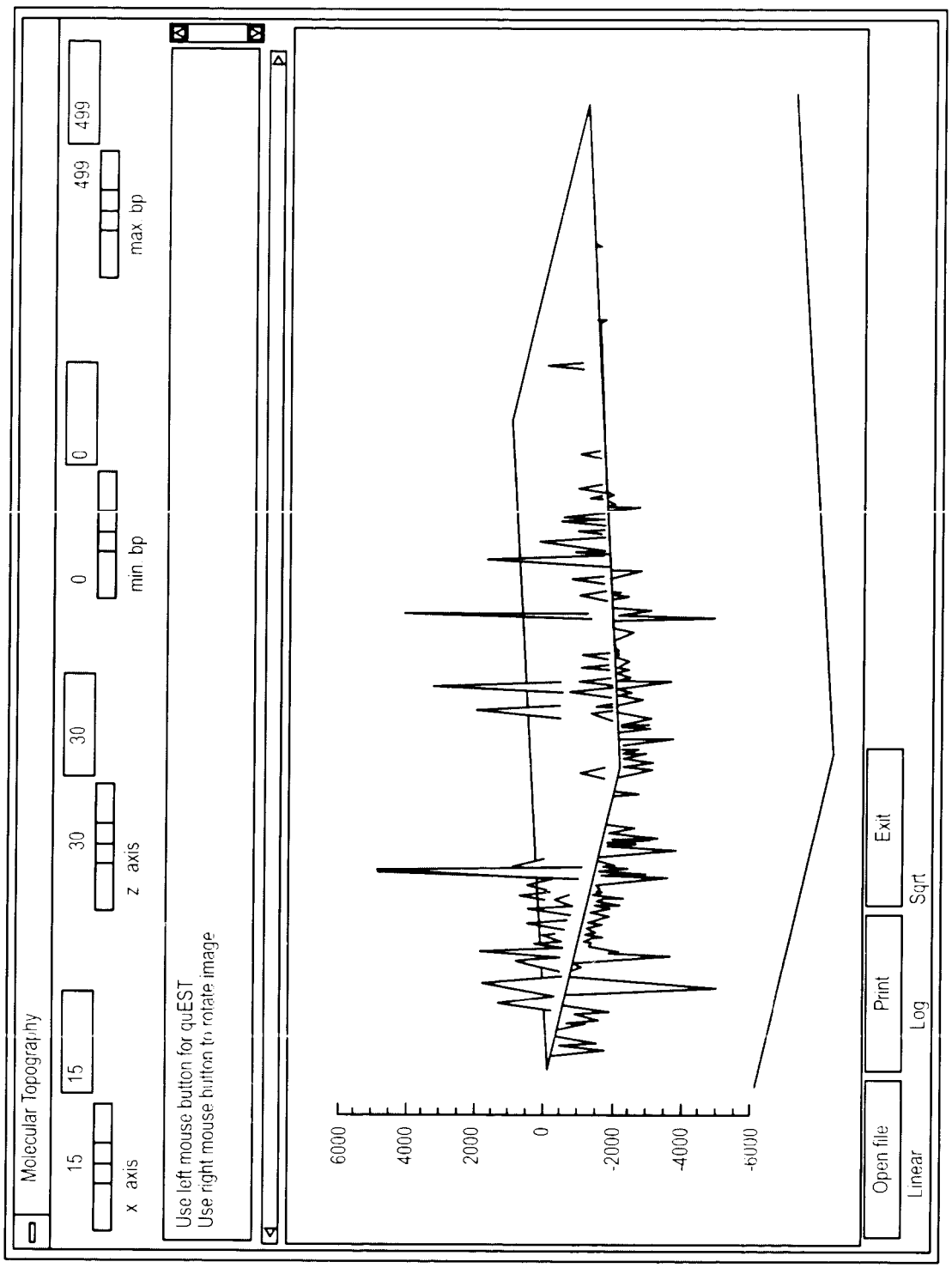

FIG. 4F is a picture of a differential molecular topography displayed in an interactive window, showing access to linked information for a chosen peak. The chosen peak is topped by a horizontal line. A descriptive excerpt of the linked information is displayed directly above the topography, indicating a database Accession Number for a DNA sequence that contains a fragment matching that of the peak.

Figure 5:
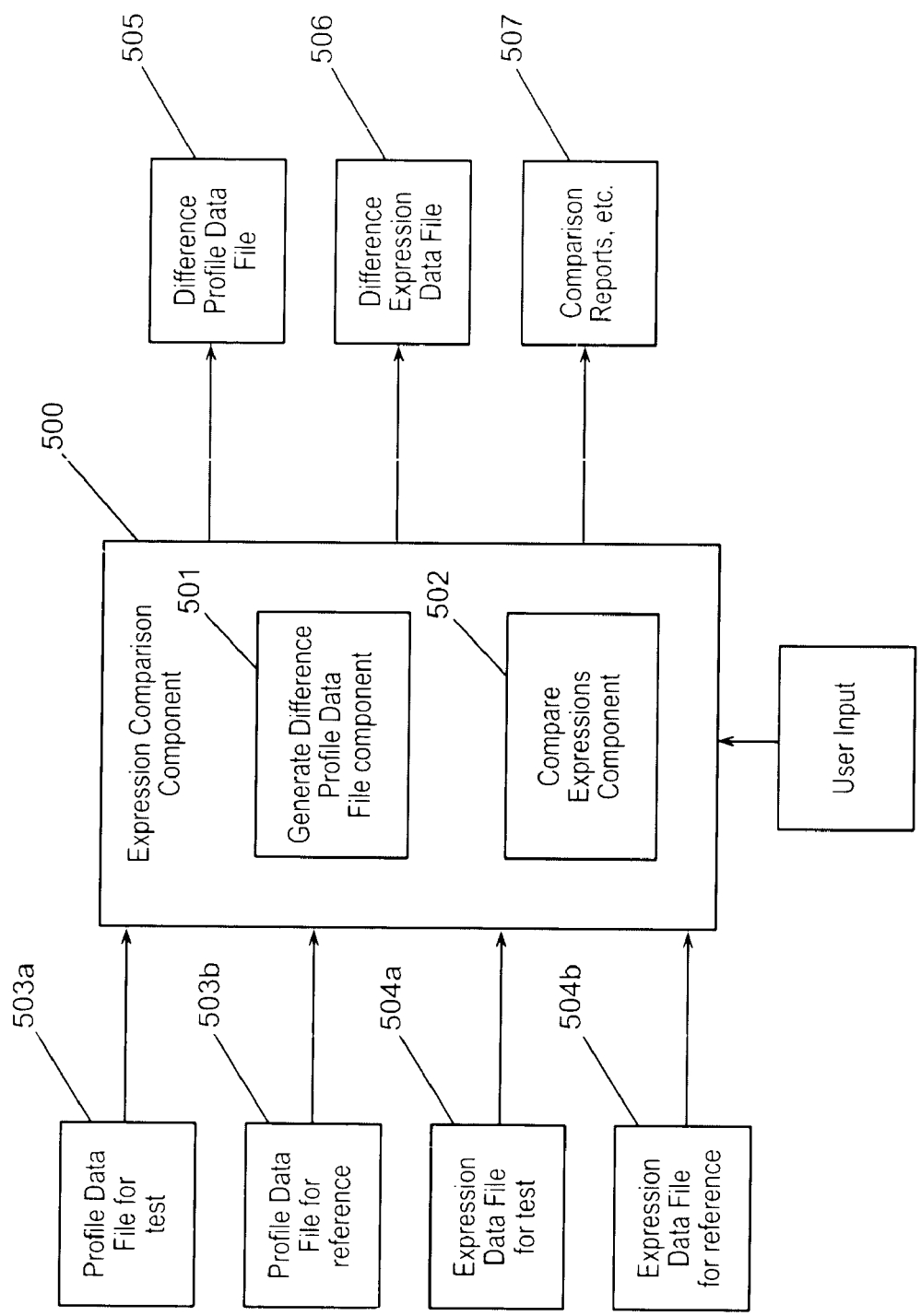
FIG. 5 is a block diagram of an expression comparison component.

FIG. 5 is a block diagram of an expression comparison component 500. The expression comparison component 500 includes a generate differential profile file sub-component 501 and a compare expressions sub-component 502. The expression comparison component 500 inputs a representation of gene expression profile of two samples, such as a test sample and a reference sample represented by files 503a and 503b, and determines whether the expressions are similar and generates differential data files.

The input that describes the expression can be in various formats, such as the table files, profile files (503a, 503b), or the expression data files (504a, 504b). In the preferred embodiment, the expression comparison component 500 receives profile files 503a–b and expression data files 504a–b for both the samples. The generate differential profile file sub-component 501 subtracts the quantities in the profile files to generate a difference profile file 505 and a difference expression data file 506.

The compare expressions sub-component 502 uses various statistical analysis techniques to define similarity between samples and output the results to a comparison results or report file 507. In one embodiment, the compared peaks of two cells can be defined to have an insignificant difference when the smaller quantity is more than 50% of the larger quantity. For example, if the larger quantity is 100, and the smaller quantity is between 50 and 99, then the two peaks are defined as having an insignificant difference and are referred to as "biologically equivalent." The significance of the differences can be defined based on the particular process by which the sample data is collected. For example, a stricter definition would be that two peaks are biologically equivalent when the smaller quantity is greater than 90% of the larger quantity.

Gene expression profiles are considered similar when a certain criteria relating to all the peaks in the profile are satisfied. For example, criteria set of expression similarity is that 95% of all peaks are biologically equivalent, 95% of the non-equivalent peaks have less than four-fold difference (e.g., the smaller quantity is greater than 25% of the larger quantity), and all the peaks have less than a six-fold difference (except when one quantity is zero). An alternate criteria set for similarity is that 98% of all peaks are equivalent, 90% of non-equivalent peaks have less than a four-fold difference, and all the peaks have less than a six-fold difference. The most strict criterion is that 100% of the peaks are equivalent. Alternatively, the average difference in the non-equivalent peaks can be compared to a threshold average. Additionally, large differences can be weighted (e.g., exponentially) to emphasize non-similarity. Finally, when the profile of a test cell is compared to the profiles of multiple reference cells, the results of the comparisons can be displayed both in order of similarity or difference.

Figure 6:
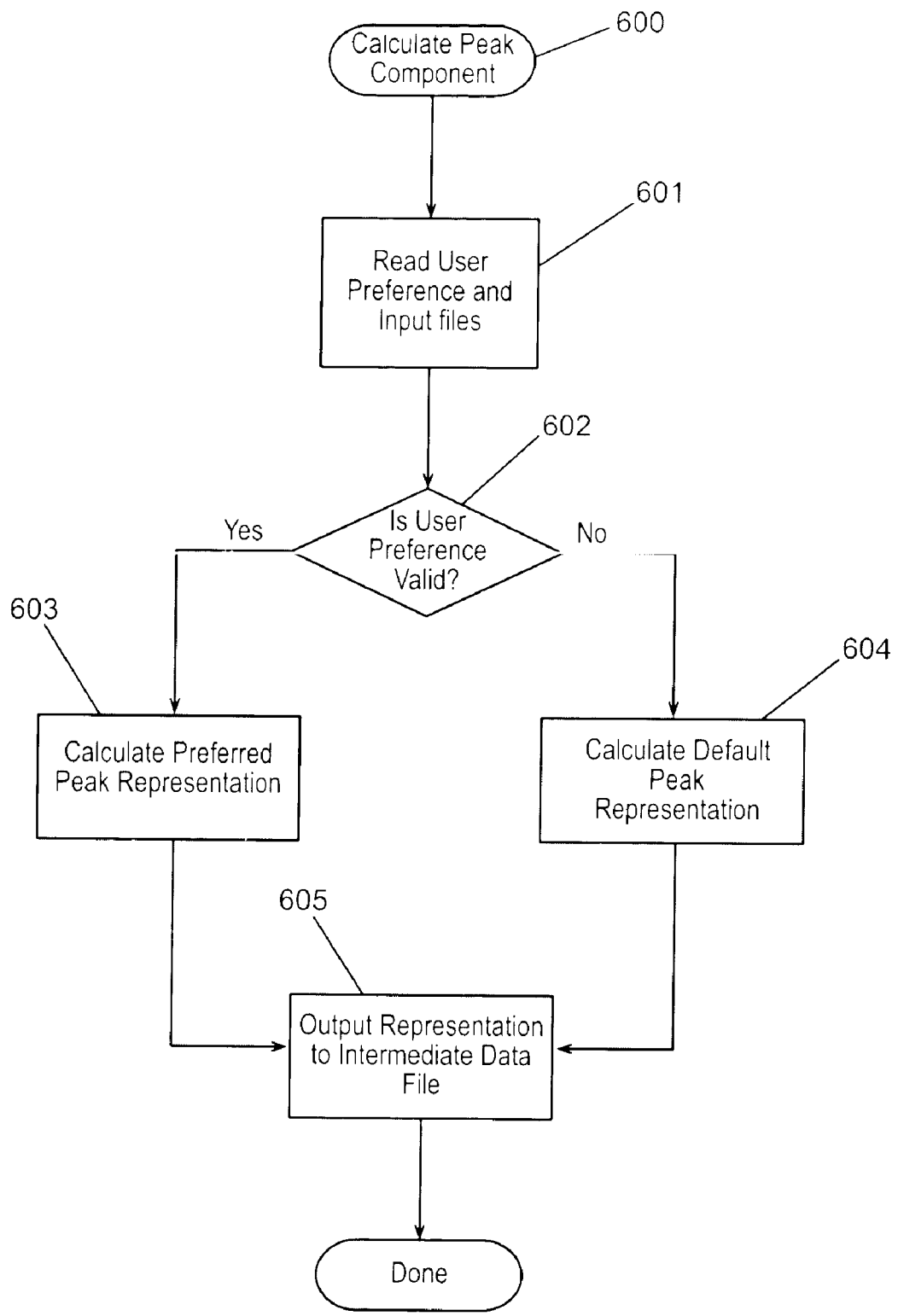
FIG. 6 is a flow diagram of a routine that calculates and generates a representation of a display peak.
Figure 7:
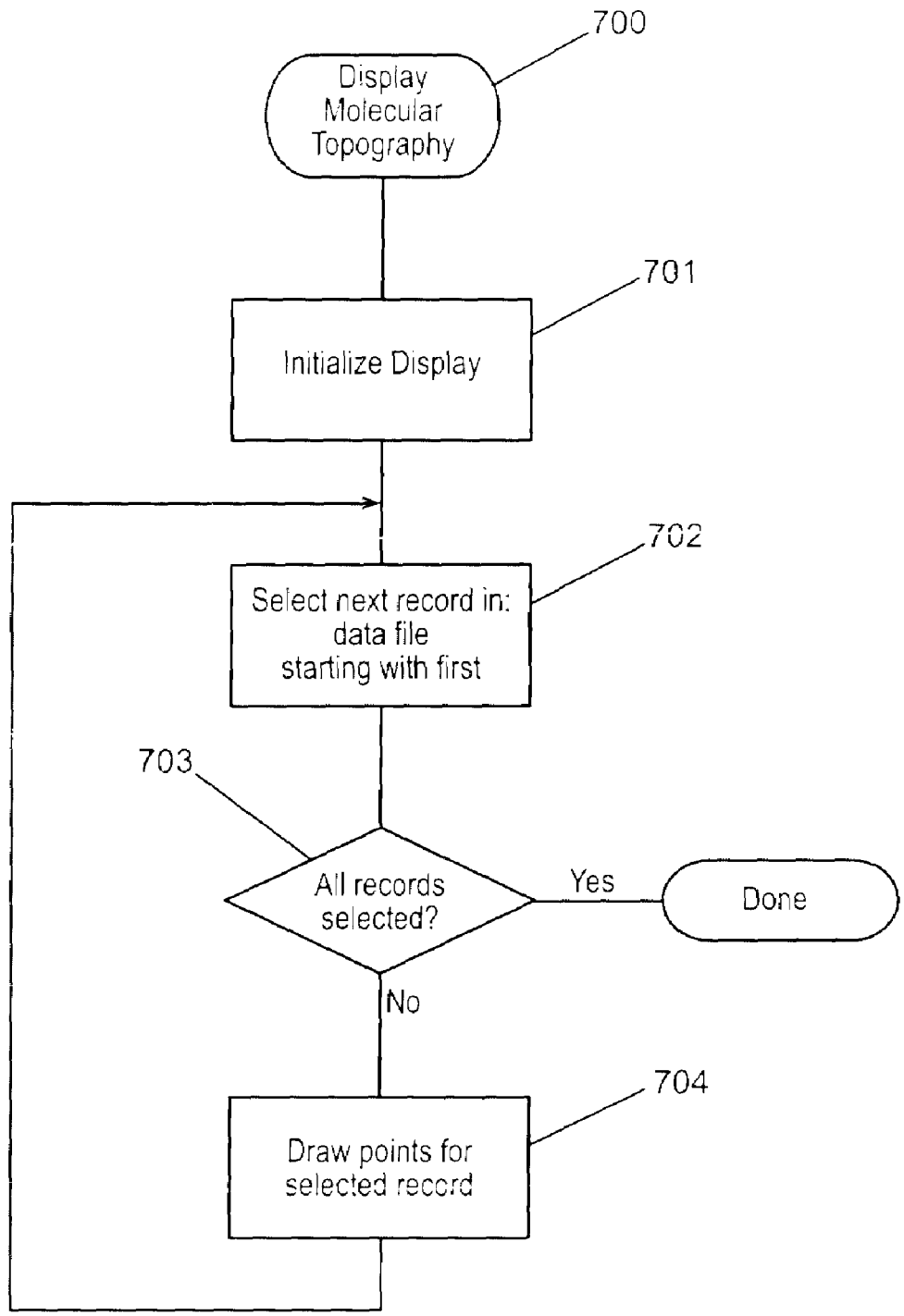
FIG. 7 is a flow diagram of a routine that displays a representation of a molecular topography.

FIGS. 6 and 7 are flow diagrams of routines to analyze and display a molecular topography. FIG. 6 shows the steps of the routine 600 that inputs an input file, such the profile data file 110, and calculates and outputs a display peak representation of all the fragments to an intermediate data file 660 that is used to visually display the molecular topography on a suitable computer display 106.

In step 601, the routine reads in the input file and an optional user input indicating a display preference of the user. In step 602, the routine checks the user input is in a valid form. If yes, the routine proceeds to step 603 and calculates a display peak representations for each fragment in accordance with the user's request. If not, the routine proceeds to step 604 to calculate a default display peak representation. In one preferred embodiment, the height of the display peak representation, is calculated to represent a polynucleotide characteristic. However, other peak properties such as the area, volume, shape, surface area, etc. can also be calculated to indicate a polynucleotide characteristic or a quantity of the polynucleotide.

In step 605, the routine writes out output records to the intermediate data file 660 so that each record contains the co-ordinates defining the peaks for each fragment in a display. In other words, all the records together constitute a set of points defining a graphical representation suitable for display. The intermediate data file 660 is used by the display molecular topology component 103 to graphically display a molecular topograph.

It is to be understood that the intermediate data file 660 could include pipes or other conventional means of inter-process communication and is not limited to a disk file. Such alternative inter-process communications methods are well known to persons skilled in the relevant art and, therefore, the choice of an optimal method of inter-process communication is a design choice that balances available computer resources with application needs.

Typically, the display 106 is a visual display such as a computer screen that allows interaction with a user. However, it is to be understood that the display could include other non-interactive displays such as a printer, or other non-visual displays such as an image or data file that is suitable for further processing.

FIG. 7 shows the steps of routine 700 that is passed the intermediate data file 660 containing a representation of a display that is generated from the gene expression profiles of the sample. That is, routine 700 is an exemplary embodiment of the display molecular topography component 103.

In step 701, the routine initializes the display 106 for the molecular topography. The initialization may include the clearing of the display and the drawing of and labeling of the various axes. In step 702, the routine selects the next record in the data file 660 starting with the first record. In step 703, if all the records have already been selected, then the routine is done, else the routine continues at step 704. In step 704, the routine draws a peak for the selected record on the display. In one display representation, the X-axis corresponds to the anchor/restriction enzyme, the Y-axis corresponds to the length, and a fragment quantity is displayed as a vertical peak along the Z-axis.

This present system can also be used to display a differential molecular topography. The system can also generate the difference profile file 505, as discussed above, so that the quantity represents a positive or negative difference between quantities of two profiles. The negative quantities can be displayed as peaks below the X-Y plane. Alternatively, negative quantities could be displayed in varying intensities of a first set of colors and positive quantities can be displayed in varying intensities of a different set of color.

Figure 8:
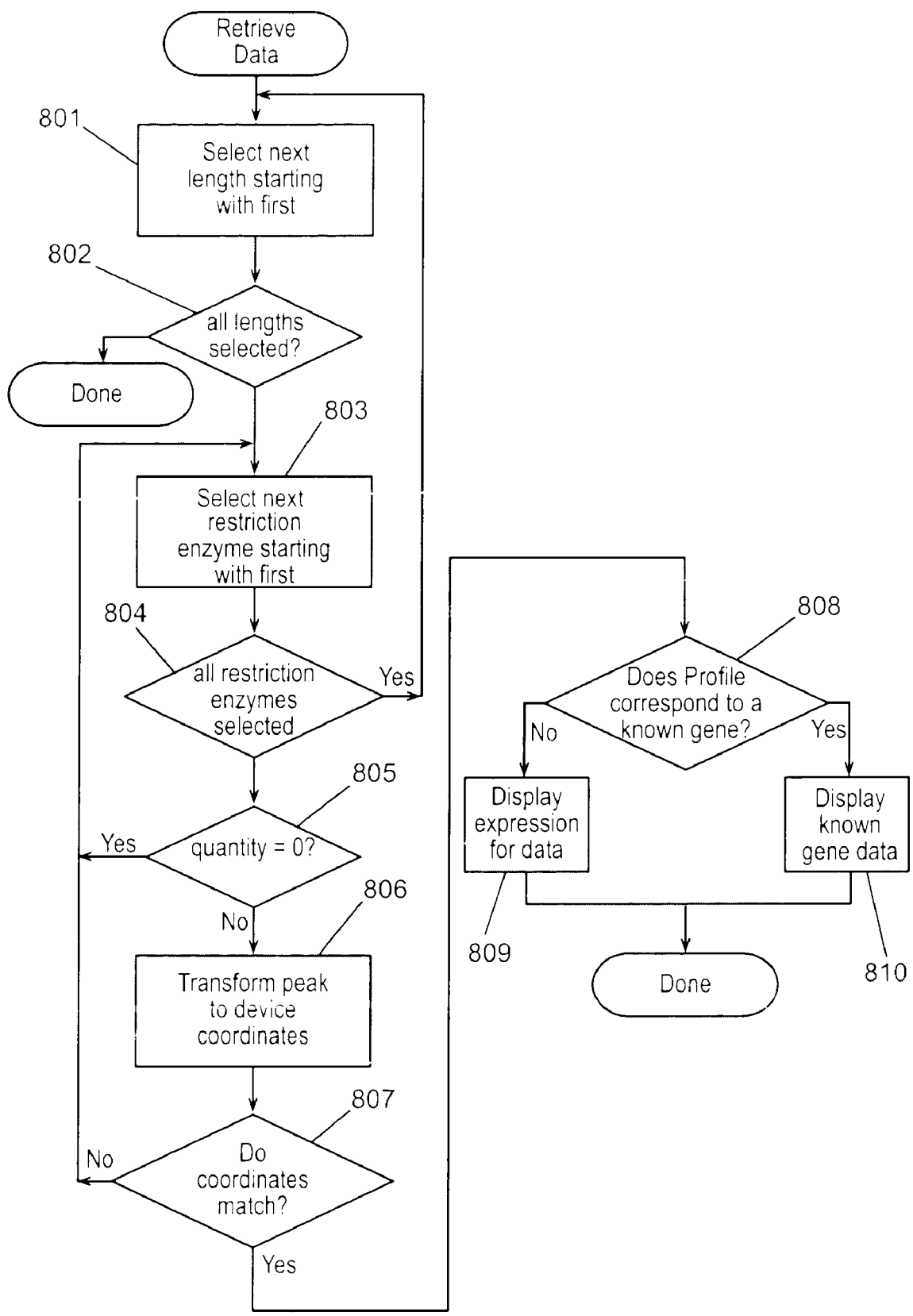
FIG. 8 is a flow diagram of a routine that retrieves additional data for a peak displayed molecular topography.

FIG. 8 is a flow diagram of an exemplary routine to retrieve additional data when a molecular topography is displayed. In one embodiment, the user indicates to retrieve additional data by selecting (e.g., with a mouse) a peak that is displayed as part of the molecular topography. This routine identifies the polynucleotide fragment by determining the length and associated anchor/restriction enzyme corresponding to that peak. If there is a known gene for that length and anchor/restriction enzyme combination, then information for the known gene is displayed. That is, for example, this routine is passed the X-Y device coordinates that correspond to the peak the user selected.

In steps 801–805, the routine loops attempting to determine the length and anchor/restriction enzyme combination which correspond to the X-Y device coordinates. In step 801, the routine selects the next fragment length starting with the shortest. In step 802, if all the lengths have already been selected, then an error has occurred because the X-Y device coordinates correspond to no peak and the routine is done, else the routine continues at step 803. In step 803, the routine selects the next anchor/restriction enzyme combination starting with the first. In step 804, if all the anchor/restriction enzyme combinations have been selected for the selected length, then the routine loops to step 801 to select the next length, else the routine continues at step 805. In step 805, if the quantity of the fragment corresponding to the selected length and the selected anchor/restriction enzyme combination is 0, then the routine loops to step 803 to select the next anchor/restriction enzyme combination, else the routine continues at step 806.

In step 806, the routine transforms the location of the peak of a selected length and the selected anchor/restriction enzyme combination to determine peak co-ordinates suitable for visual display. In step 807, if the passed X-Y display coordinates are near the transformed coordinates, then the routine continues at step 808, else the routine loops to step 803 to select the next anchor/restriction enzyme combination. In step 808, if the selected length and the selected anchor/restriction enzyme correspond to a known gene as identified in the known gene file 112, then the routine continues to step 810, else the routine continues at step 809. In step 809, the routine displays the expression data from the expression data file for the sample cell and completes the routine. In step 810, the routine displays the known gene data for the sample cell from the known gene file for the sample cell and completes the routine.

Figure 9:
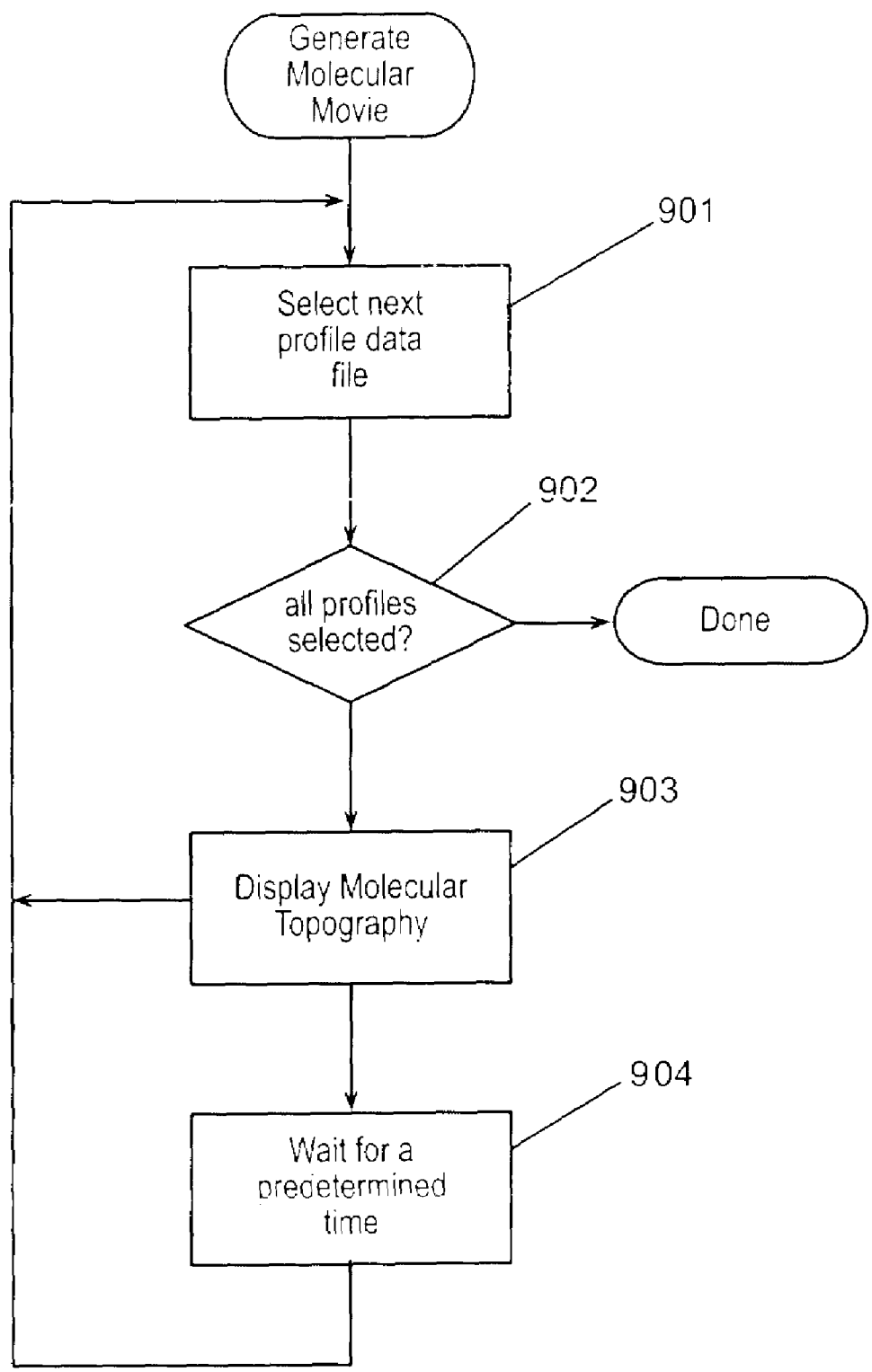
FIG. 9 is a flow diagram of a routine for generating a molecular movie.

FIG. 9 is a flow diagram of an exemplary routine to generate a molecular movie. This routine is passed multiple profile data files. The routine then displays the molecular topography for each profile data file in sequence. In step 901, the routine selects the next profile data file starting with the first. In step 902, if all the profile data files have already been selected, then the routine is done, else the routine continues at step 903. In step 903, the routine invokes the routine 700 to display the molecular topography for the selected profile data file. In step 904, the routine waits a predetermined amount of time to allow the researcher to view the visual representations of the profile data files. The amount of the wait time is configurable. Alternatively, the next molecular topography can be displayed when the user indicates a selection. The routine then loops to step 901 to select the next profile data file.

Figure 10:
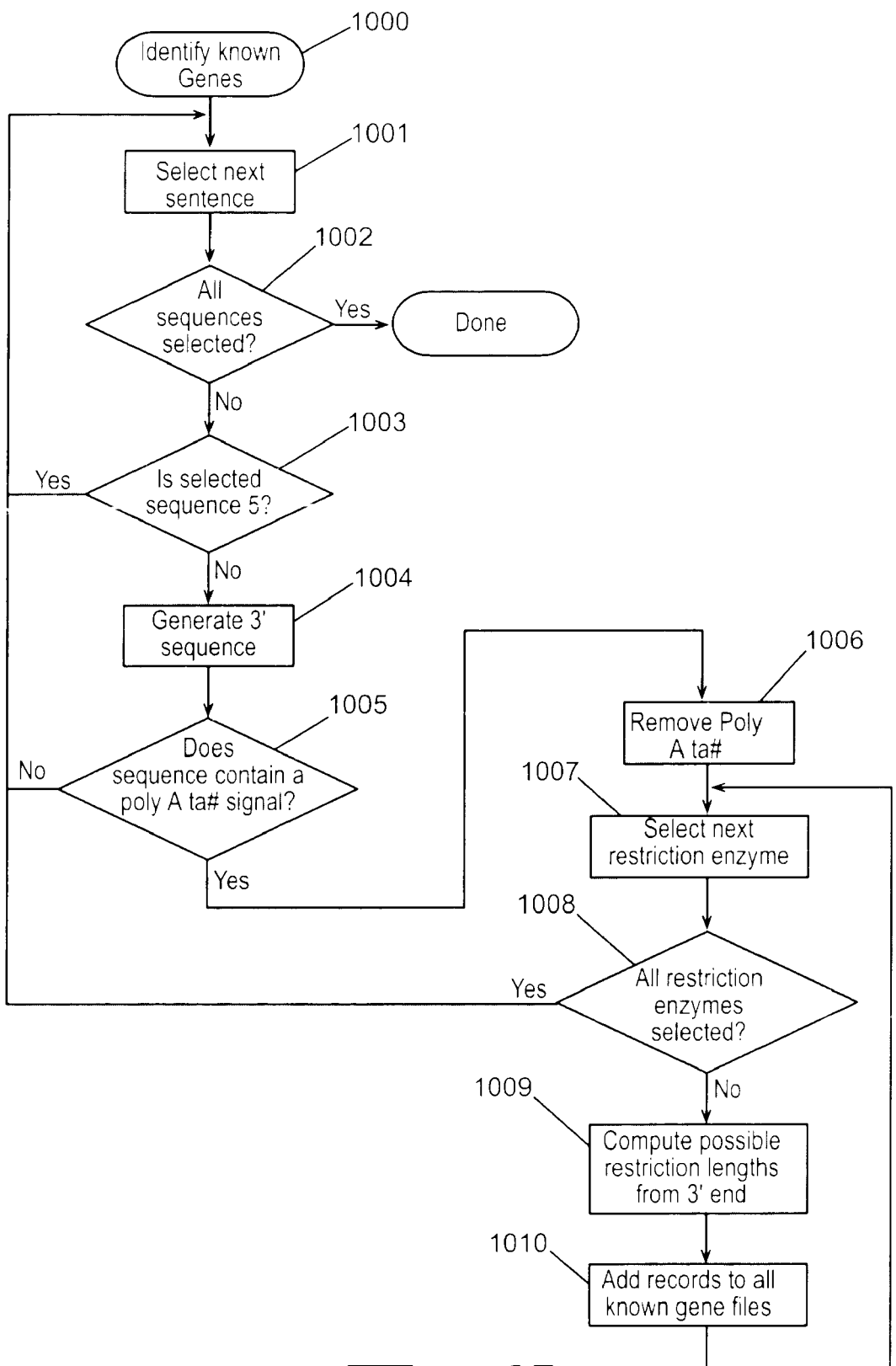
FIG. 10 is a flow diagram of a routine for identifying DNA sequences and characterized genes in a DNA sequence database that correspond to peaks in a molecular topography display, and for retrieving and displaying known information about the identified DNA sequences or genes.

FIG. 10 is a flow diagram of an exemplary routine to identify known genes from a gene sequence collection database. That is, routine 100 is one embodiment of the identify known genes component 209.

In step 1001, the routine selects the next sequence in the database starting from a first. In step 1002, if all the sequences have already been selected, then the routine is done, else the routine continues at step 1003. In step 1003, if the selected sequence is indicated as 5', then the routine continues at step 1001, else the routine continues at step 1004. In step 1004, the routine retrieves the 3' sequence. In step 1005, if the retrieved 3' sequence contains poly A sequence, then the routine continues at step 1006, else the routine loops to step 1001 to select the next sequence. In step 1006, the routine removes the polyA tail. In steps 1007–1010, the routine loops through each anchor/restriction enzyme combination and determines all possible lengths of cuts for that anchor/restriction enzyme combination on the selected sequence. In step 1007, the routine selects the next anchor/restriction enzyme combination starting with the first. In step 1008, if all the anchor/restriction enzyme combinations have already been selected, then the routine loops to step 1001 to select the next sequence in the collection database, else the routine continues at step 1009. In step 1009, the routine computes all possible lengths of cuts from the 3' end for the selected anchor/restriction enzyme combination. In step 1010, the routine adds a record to the all known gene file for each length of a cut for the selected anchor/restriction enzyme combination and loops to step 1007 to select the next anchor/restriction enzyme combination.

Figure 11:
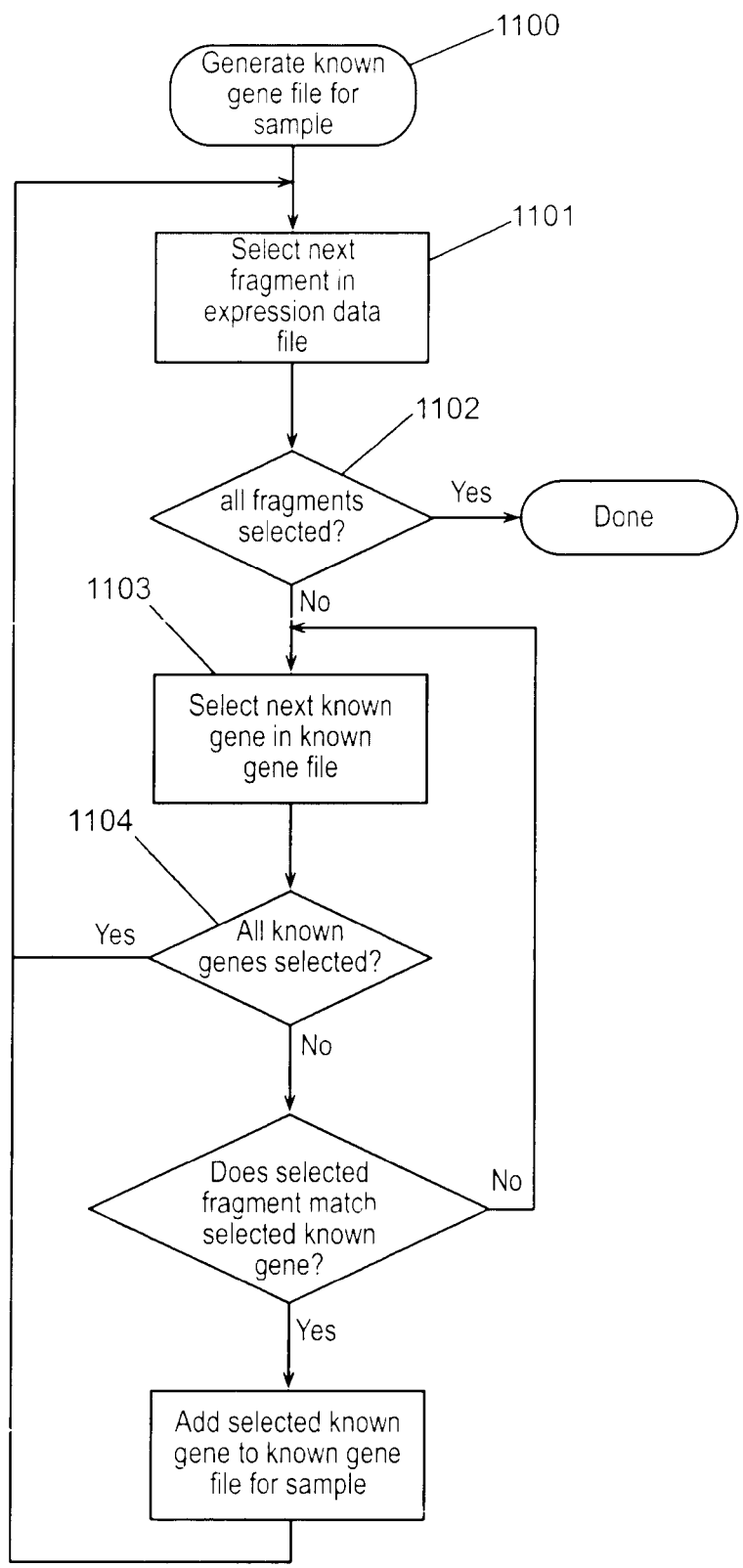
FIG. 11 is a flow diagram of a routine for generating a known sample gene file that contains DNA sequences or genes identified in one or more databases as corresponding to a peak or peaks in a molecular topography.

FIG. 11 is a flow diagram of an exemplary routine 1100 to generate a known gene file for a sample. That is, routine 100 is one embodiment of the generate known gene file for sample component 211.

The routine 1100 inputs the expression data file 111 for a sample cell and the all known genes file 212. The routine 1100 determines which fragments of the gene expression profile for the sample cell correspond to known genes in the all known gene file 212. The routine 1100 outputs to the known gene file 112 for the sample cell which contains data describing all such known genes.

In step 1101, the routine selects the next fragment (i.e., record) in the expression data file 111. In step 1102, if all the fragments in the expression data file have already been selected, then the routine is done, else the routine continues at step 1103. In step 1103–1106, the routine loops selecting each known gene (i.e., record) in the all known gene file 212 until all the known genes are selected or a match with the selected fragment is found. In step 1103, the routine selects the next known gene in the all known gene file 212. In step 1104, if all the known genes have already been selected, then the routine 1100 loops to step 1101 to select the next fragment in the expression data file 111, else the routine continues at step 1105. In step 1105, if the selected fragment matches the selected known gene, then the routine continues at step 1106, else the routine loops to step 1103 to select the next known gene. In step 1106, the routine adds a record for the known gene to the known gene file 112 for the sample cell and loops to step 1101 to select the next fragment.

The foregoing provides a general description of the invention with reference to several more specific embodiments. It does not exhaustively describe the invention. Further aspects and embodiments of the invention will be apparent to those skilled in the art from consideration of the specification, figures and claims of this disclosure, together with their own knowledge of the arts to which it pertains. The disclosure of all publications cited above are expressly incorporated herein by reference in their entireties to the same extent as if each were incorporated by reference individually. Further, the disclosure of Provisional Application 60/059,727, filed Sep. 23, 1997, for which benefit under 35 USC §119 is claimed, is expressly incorporated herein in its entirety, including the specification, claims, figures and abstract.

What is claimed is:

1. A method in a computer system for generating a graphic display for visualization of gene expression in a molecular topography, comprising:
   providing a first set of data, the data comprising gene expression measurements and descriptive information for a first plurality of polynucleotides;
   defining an X-Y plane having a first axis corresponding to sequence identifiers and a second axis corresponding to polynucleotide sizes;
   generating a first gene expression profile within the X-Y plane for the first plurality of polynucleotides, the first profile comprising a plurality of peaks with each peak corresponding to a polynucleotide, the peak defined by:
   (i) a first value comprising a sequence identifier for the polynucleotide;
   (ii) a second value comprising a measure of size of the polynucleotide, wherein an intersection between the first value and the second value defines a point within the X-Y plane; and
   (iii) at the point, plotting along a Z-axis intersecting the X-Y plane a third value that is a measure of quantity of the polynucleotide;
   wherein the plurality of peaks is generated for the first plurality of polynucleotides so that the graphic display comprises a molecular topography of gene expression.

2. The method of claim 1, further comprising:
   providing a second set of data comprising gene expression measurements and descriptive information for a second plurality of polynucleotides;
   generating a second gene expression profile within the X-Y plane for the second plurality of polynucleotides;
   comparing the first and second gene expression profiles to generate a differential gene expression profile;
   wherein the graphic display comprises the molecular topography of differential gene expression.

3. The method of claim 2, wherein one of the first and second sets of data corresponds to a reference sample and the other of the first and second sets of data corresponds to a test sample.

4. The method of claim 3, wherein the differential gene expression profile is diagnostic of a condition or disease.

5. The method of claim 1, further comprising:
providing a plurality of subsequent sets of data for the same or comparable sample as the first set of data in a temporal succession; and
generating and displaying gene expression profiles for each subsequent set of data to observe dynamic changes in gene expression over time.

6. The method of claim 5, wherein the subsequent sets of data are taken from samples comprising cells undergoing one or more of growth, differentiation and division.

7. The method of claim 5, wherein the subsequent sets of data are taken from samples comprising cells undergoing disease process and/or therapy.

8. The method of claim 2, further comprising:
providing a plurality of subsequent sets of data for the same or comparable sample as the first and second sets of data in a temporal succession; and
generating and displaying differential gene expression profiles for each subsequent set of data to observe dynamic changes in differential gene expression over time.

9. The method of claim 8, wherein the subsequent sets of data are taken from samples comprising cells undergoing one or more of growth, differentiation and division.

10. The method of claim 8, wherein the subsequent sets of data are taken from samples comprising cells undergoing disease process and/or therapy.

11. A method in a computer system for generating a graphic display for visualization of gene expression data, comprising:
providing a first set of data, the data comprising gene expression measurements and descriptive information for a first plurality of polynucleotides;
defining an X-Y plane having a first axis corresponding to sequence identifiers and a second axis corresponding to polynucleotide sizes;
plotting within the X-Y plane a plurality of points corresponding to the first plurality of polynucleotides according to their sequence identifiers and polynucleotide sizes; and
for each point within the plane, plotting along a Z-axis intersecting the X-Y plane a measured value corresponding to a quantity of mRNA produced for the polynucleotide plotted at the point so that a peak extending from the X-Y plane is generated;
wherein the graphic display comprises a three-dimensional plot representative of gene expression for the first plurality of polynucleotides.

12. The method of claim 11, further comprising:
providing a second set of data comprising gene expression measurements and descriptive information for a second plurality of polynucleotides;
generating a second gene expression profile within the X-Y plane for the second plurality of polynucleotides;
comparing the first and second gene expression profiles to generate a differential gene expression profile;
wherein the graphic display comprises the molecular topography of differential gene expression.

13. The method of claim 12, wherein one of the first and second sets of data corresponds to a reference sample and the other of the first and second sets of data corresponds to a test sample.

14. The method of claim 13, wherein the differential gene expression profile is diagnostic of a condition or disease.

15. The method of claim 11, further comprising:
providing a plurality of subsequent sets of data for the same or comparable sample as the first set of data in a temporal succession; and
generating and displaying gene expression profiles for each subsequent set of data to observe dynamic changes in gene expression over time.

16. The method of claim 15, wherein the subsequent sets of data are taken from samples comprising cells undergoing one or more of growth, differentiation and division.

17. The method of claim 15, wherein the subsequent sets of data are taken from samples comprising cells undergoing disease process.

18. The method of claim 12, further comprising:
providing a plurality of subsequent sets of data for the same or comparable sample as the first and second sets of data in a temporal succession; and
generating and displaying differential gene expression profiles for each subsequent set of data to observe dynamic changes in differential gene expression over time.

19. The method of claim 18, wherein the subsequent sets of data are taken from samples comprising cells undergoing one or more of growth, differentiation and division.

20. The method of claim 18, wherein the subsequent sets of data are taken from samples comprising cells undergoing disease process and/or therapy.

* * * * *